US008418897B1

(12) United States Patent
Young

(10) Patent No.: US 8,418,897 B1
(45) Date of Patent: Apr. 16, 2013

(54) BODY WORN CHILD CARRIER

(76) Inventor: Anthony Young, Alameda, CA (US)

( * ) Notice: Subject to any disclaimer, the term of this patent is extended or adjusted under 35 U.S.C. 154(b) by 0 days.

(21) Appl. No.: 13/594,871

(22) Filed: Aug. 27, 2012

(51) Int. Cl.
*A37D 13/02* (2006.01)
*A61F 5/37* (2006.01)

(52) U.S. Cl.
USPC ........... 224/160; 224/159; 224/158; 224/628; 224/638; 602/4

(58) Field of Classification Search .................. 224/259, 224/266, 267, 623, 624, 638, 639, 158–161, 224/628, 922, 260–262, 184; 294/25; 602/4, 602/6; 2/44, 45, 256, 255, 258, 259, 260; D3/213, 214
See application file for complete search history.

(56) References Cited

U.S. PATENT DOCUMENTS

| | | | |
|---|---|---|---|
| 9,828 A | 7/1853 | Day | |
| 114,615 A | 5/1871 | Smitley | |
| 278,437 A | 5/1883 | Lancaster | |
| 522,018 A | 6/1894 | Kehlenbeok | |
| 554,019 A | 2/1896 | Collins | |
| 679,288 A | 7/1901 | Bohrer | |
| 1,490,381 A | 4/1924 | Gobar | |
| 1,535,208 A | 4/1925 | Drennan | |
| 1,760,443 A | 5/1930 | Scheidegger | |
| 1,879,480 A * | 9/1932 | Pures | 224/260 |
| 2,358,551 A | 9/1944 | Beaton | |
| 2,460,589 A | 2/1949 | Lewis | |
| 2,560,243 A * | 7/1951 | Peterson | 602/4 |
| 3,144,230 A * | 8/1964 | Brooks | 248/102 |
| 3,297,026 A | 1/1967 | Van Pelt | |
| 3,307,538 A | 3/1967 | Groll | |
| 3,507,311 A | 4/1970 | Wilson | |
| 3,547,322 A * | 12/1970 | Dawson et al. | 224/148.2 |
| 3,587,952 A | 6/1971 | Higuchi | |

(Continued)

FOREIGN PATENT DOCUMENTS

| | | |
|---|---|---|
| AU | 2010923 A1 | 1/2004 |
| CA | 2010923 C | 3/1995 |

(Continued)

OTHER PUBLICATIONS

Martin, Positioning Manual, Mar. 2, 2012, pp. 10-12, Officina di Protest Trento SpA (OPT), Caliano, Italy.

(Continued)

*Primary Examiner* — Nathan J Newhouse
*Assistant Examiner* — Matthew Theis
(74) *Attorney, Agent, or Firm* — Stone Creek Services LLC; Alan M Flum

(57) ABSTRACT

Disclosed is a child-carrying device designed to help a wearer carry a child, baby, infant, or toddler in their arms and accommodate a variety of holding positions. The child-carrying device can include a dual-shoulder harness, a rigid bar secured transversely between frontal strap portions of the harness, and a movable hand/wrist support assembly attached to the bar in a manner that it can freely move along the bar toward either side of the front of the wearer's rib cage, and optionally rotate about the bar. In one embodiment, to use the device, the wearer picks up a child, puts an arm under the child to support the child's weight, and then slips his hand through the hand/wrist support assembly in the form of a hand/wrist sling assembly; once in this position, only minimal exertion is required to carry the child.

14 Claims, 32 Drawing Sheets

U.S. PATENT DOCUMENTS

| | | | |
|---|---|---|---|
| 4,214,579 A | | 7/1980 | Ford |
| 4,319,704 A | | 3/1982 | Rosen |
| 4,355,635 A | | 10/1982 | Bihl et al. |
| 4,436,233 A | | 3/1984 | Hill |
| 4,480,775 A | * | 11/1984 | Stanford ............ 224/635 |
| 4,491,129 A | * | 1/1985 | Lockwood ............ 602/4 |
| 4,651,349 A | | 3/1987 | Heiler |
| 4,750,653 A | | 6/1988 | Prunty |
| 4,751,923 A | | 6/1988 | Marino |
| 4,815,639 A | | 3/1989 | Lehman |
| 5,020,709 A | | 6/1991 | Hoaglan |
| 5,044,321 A | * | 9/1991 | Selph ............ 119/416 |
| 5,141,488 A | | 8/1992 | Schrader |
| 5,307,967 A | * | 5/1994 | Seals ............ 224/257 |
| 5,358,470 A | | 10/1994 | Johnson |
| 5,511,707 A | | 4/1996 | Reichert |
| 5,651,143 A | | 7/1997 | Zehrung |
| 5,775,770 A | | 7/1998 | Tunney |
| 5,881,487 A | * | 3/1999 | Chalker ............ 42/85 |
| 6,040,509 A | * | 3/2000 | Fanella ............ 84/280 |
| 6,089,425 A | | 7/2000 | Fair et al. |
| 6,095,993 A | | 8/2000 | Hawkins |
| 6,199,731 B1 | * | 3/2001 | Lehoux ............ 224/260 |
| 6,206,787 B1 | | 3/2001 | Kleppen |
| 6,217,537 B1 | | 4/2001 | Root |
| 6,364,183 B1 | | 4/2002 | Barnard |
| 6,550,653 B2 | * | 4/2003 | Matthews ............ 224/250 |
| 6,595,396 B2 | | 7/2003 | Cummings et al. |
| 6,883,691 B2 | | 4/2005 | Pratt et al. |
| 6,974,429 B2 | * | 12/2005 | Moore et al. ............ 602/4 |
| 6,979,303 B2 | | 12/2005 | Jestrabek-Hart |
| 7,037,281 B1 | | 5/2006 | Jeffrey et al. |
| D574,579 S | * | 8/2008 | Kang ............ D2/840 |
| 7,591,401 B2 | | 9/2009 | Sandler |
| 7,669,743 B2 | | 3/2010 | Bruton |
| 7,686,195 B2 | | 3/2010 | Bangert |
| 7,749,179 B2 | | 7/2010 | Hargrave |
| 7,757,911 B2 | | 7/2010 | Barker |
| D648,521 S | | 11/2011 | Higuchi |
| 2002/0162864 A1 | | 11/2002 | Grunwald |
| 2003/0220168 A1 | * | 11/2003 | Perry ............ 475/276 |
| 2004/0149790 A1 | | 8/2004 | Kassai et al. |
| 2004/0211799 A1 | | 10/2004 | Loughman |
| 2004/0250332 A1 | * | 12/2004 | Tadin ............ 2/94 |
| 2005/0010147 A1 | | 1/2005 | Kazmierczak et al. |
| 2005/0155996 A1 | | 7/2005 | Hiscocks |
| 2005/0161479 A1 | | 7/2005 | Licsko |
| 2006/0208018 A1 | | 9/2006 | Bruton |
| 2006/0258966 A1 | | 11/2006 | Hargrave et al. |
| 2008/0047987 A1 | | 2/2008 | Price |
| 2008/0190972 A1 | | 8/2008 | Gray |
| 2009/0302075 A1 | | 12/2009 | Trainer |
| 2010/0282808 A1 | | 11/2010 | Debnam et al. |
| 2011/0034841 A1 | | 2/2011 | Richard |
| 2011/0120295 A1 | | 5/2011 | Carter |
| 2011/0226822 A1 | | 9/2011 | Higuchi |
| 2012/0000947 A1 | | 1/2012 | Ashley |
| 2012/0074182 A1 | | 3/2012 | Harris |
| 2012/0085795 A1 | | 4/2012 | Peng |

FOREIGN PATENT DOCUMENTS

| | | |
|---|---|---|
| CA | 2433252 A1 | 12/2004 |
| CH | 603153 A5 | 8/1978 |
| CN | 101433414 B | 12/2011 |
| EP | 1947978 B1 | 4/2011 |
| FR | 2674114 A1 | 9/1992 |
| GB | 1560260 A | 1/1980 |
| JP | 2004181268 A | 7/2004 |
| JP | 2004358002 A | 12/2004 |
| JP | 2005323975 A | 11/2005 |
| JP | 2006341080 A | 12/2006 |
| JP | 2008055117 A | 3/2008 |
| JP | 4399644 B9 | 11/2009 |
| JP | 4772499 B9 | 7/2011 |
| JP | 4874613 B2 | 2/2012 |
| WO | 2011046493 A1 | 4/2011 |
| WO | 2012081013 A1 | 6/2012 |

OTHER PUBLICATIONS

Remember Piggyback Rides as a Kid?The Piggyback Rider, Accessed on the Internet on Jul. 26, 2012: http://piggybackrider.com/ride-the-bar.

Piggyback Rider Child Safety Harness, Model: NILOC, Features, Accessed on the Internet on Jul. 26, 2012: http://piggybackrider.com/features.

Boba Adjustable Replacement Footstraps, Boba Inc. Boulder, CO, Accessed on the Internet on Jul. 26, 2012: http://store.bobafamily.com/accessories/.

HR-3 Delux Harness, Manta Industries & Highseas Millwork, Privateer Divers, LLC, accessed on the Internet on Jul. 24, 2012: http://www.privateerdivers.com/wp-content/uploads/2011/01/HR-3.-426x600.jpg.

Karin Frost, The Ergo Baby Carrier (Instruction Manual), Jul. 2005, The Ergo Baby Carrier, Inc.

Standard Hemi Arm Sling NC16006, Jun. 2011, North Coast Medical, Gilroy, CA, US.

Pro AbDominator Ab Slings, Shapeupshop.com, accessed on the internet: http://www.shapeupshop.com/fitness/abs/slings.htm on Jul. 5, 2012.

Mary Vining Radomski and Caterine A. Trombly, Occupational Therapy for Physical Dysfunction, Mar. 2007, pp. 444-445, Lippincott Williams & Wilkins; Sixth edition, Baltimore, MD.

Span America Thoracotomy Arm Sling, Accessed on the Internet on Jul. 5, 2012: http://www.sears.com/shc/s/p_10153_12605_SPM730640801P.

Aofeite Immobizing Arm Sling with FDA, CE, Alibaba.com, Accessed on the Internet on Jul. 5, 2012: http://www.alibaba.com/product-gs/441106472/AOFEITE_immobilizing_arm_sling_with_FDA.html.

Folding Arm Sling Suspension Free, Rehabmart.com, Accessed on the Internet on Jul. 5, 2012: http://www.rehabmart.com/product/folding-arm-suspension- frame-9888.html.

Pouch Arm Sling Adjustable, Alibaba.com, Accessed on the Internet on Jul. 5, 2012: http://www.alibaba.com/product-gs/340381439/Pouch_Arm_Sling_Adjustable_Special_html.

CY-FS05A Hanging Ab Straps Ab Arm Sling for perfect pull up, chin up—Yongkang Chiyu Industrial and Trading Co., Ltd., Furkey, accessed on the internet on Jul. 6, 2012 at: http://chiyu.global.furkey.com/product/206579-cyfs05a-hanging-ab-straps-ab-arm-sling-for-perfec.html.

John D. Enderle, editor, Arm Mounted Carry Assistant, 2008 Engineering Senior Design Projects to Aid Persons with Disabilities, Date of Publication: 2011, pp. 140-141, Creative Learning Press, Inc. Mansfield Center, CT.

* cited by examiner

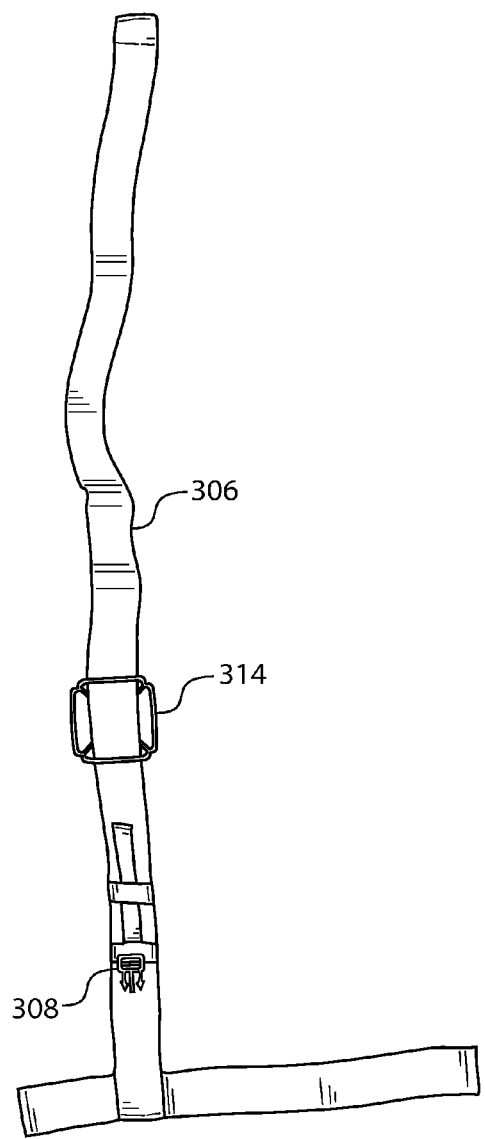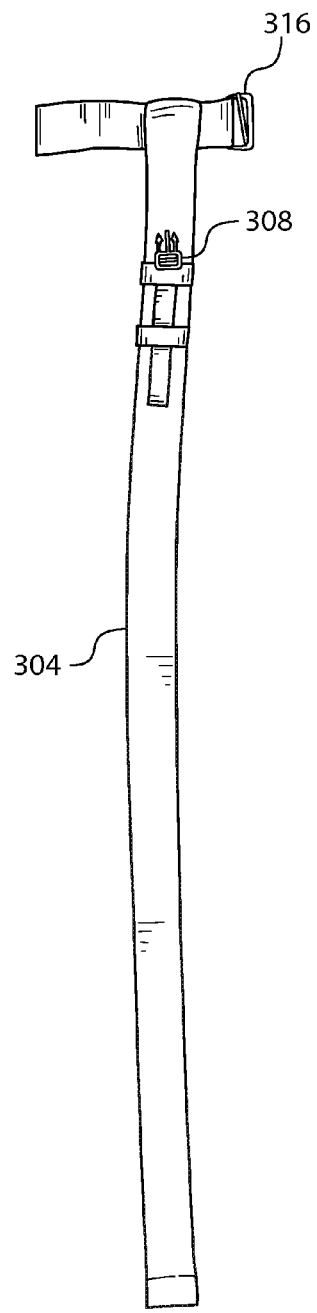
FIG. 20A                    FIG. 20B

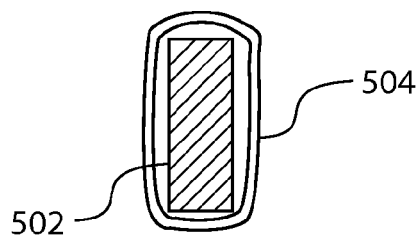
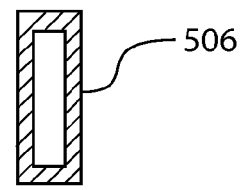
FIG. 23A    FIG. 23B
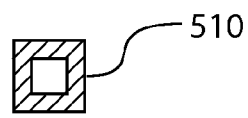
FIG. 23C    FIG. 23D
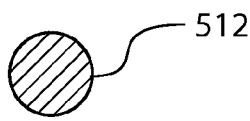
FIG. 23E    FIG. 23F
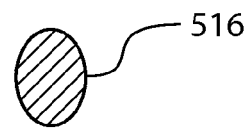
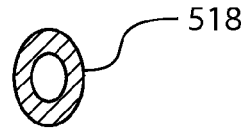
FIG. 23G    FIG. 23H

BODY WORN CHILD CARRIER

BACKGROUND

The present disclosure relates to an apparatus for assisting a wearer carrying a child, baby, or infant against their body.

Holding a child, baby, infant or toddler can be tiring. Body worn child carriers allow the wearer to tote or carry a child for extended periods of time compared to simply holding the child. Body worn child carrying devices include slings, front and rear mounted harness carriers, and hip carriers.

Many body worn child carriers suffer from one or more deficiencies. The carrier can be difficult to set up. Once set-up, changing the position of the child may be challenging and may require removing either the entire carrier or a portion of the carrier from the wearer. In addition, the carrier may not be comfortable for the wearer over extended periods, often creating pressure on the wearer's neck or shoulders; this is a particular problem with some sling-type carriers. The carrier may be uncomfortable to both the wearer and the child in hot weather. Also, carriers that have some degree of separation between child and wearer, for example, some front or rear mounted harness carriers, may lack the intimacy between child and wearer afforded by direct carrying.

SUMMARY

This Summary introduces a selection of concepts in simplified form that are described in more detail in the Description. The Summary is not intended to identify essential features or limit the scope of the claimed subject matter.

Disclosed, in several embodiments, is a device that attempts to overcome the aforementioned deficiencies described in the Background. The device can assist the wearer to support a child, baby, infant, or toddler on the wearer's arm and afford the wearer the possibility of adjusting the position of their arm along their body while holding the child.

The child-carrying device includes a dual-shoulder harness, a transversely mounted rigid bar, and a hand/wrist support assembly movable along the rigid bar. In one embodiment, the hand/wrist support assembly is a hand/wrist sling assembly. The shoulder harness includes a first shoulder strap portion passing over one shoulder and a second shoulder strap portion passing over the other shoulder of the wearer. The rigid bar is positioned transversely across the front of the wearer's rib cage and secured proximate to a first end portion of the rigid bar to the first shoulder strap portion and secured proximate to a second end portion of the rigid bar to the second shoulder strap portion. The rigid bar is made of a material strong enough resist substantial flexion under the weight of a child. A portion of each shoulder strap extends over the wearer's back, under their arm on the same side body and attaches to an end portion of the rigid bar. Depending on the configuration of the dual-shoulder harness, a stabilizing back strap can be attached transversely between each shoulder strap portion on the back of the wearer. The stabilizing back strap is detachably attached in order to accommodate the wearer putting on and removing the child-carrying device. The movable hand/wrist sling assembly includes a portion attached circumferentially around the rigid bar, and can freely move along the rigid bar to either side of the front rib cage, and partially rotate about the bar, thus accommodating a wide variety of holding positions. The rigid bar holds the first shoulder strap portion and the second shoulder strap portion apart, at a position proximate to the lateral position of the rigid bar. The inventor observed that this arrangement, combined with the rigid bar being mounted over the front of the wearer's rib cage, helps to distribute the weight more evenly over various positions of the hand/wrist sling along the rigid bar while supporting the child. To use the device, the wearer picks up the child, puts an arm under the child to support the child's weight, and then slips his hand through the strap; once in this position, only minimal exertion is required to carry the child.

In another embodiment, the shoulder strap portions are secured to each other on the front of the wearer, in part, by a transverse front strap positioned below the wearer's armpits over the front of the wearer's rib cage. The transverse front strap can be detachably attached, for example, by a detachable buckle, ladder lock, or bar slide.

In a further embodiment, the shoulder strap portions can form a cross-pattern across the wearer's back in order to provide additional stability. The bar can be detachably attached to the shoulder harness on at least one end in order to accommodate the wearer putting on and removing the child-carrying device.

In another embodiment, the rigid bar includes an aperture defining a slot along the length of the bar. A portion of the hand/wrist sling assembly includes a flanged attachment. The flanged attachment, in combination with the slot, forms a joint that allows the hand/wrist sling assembly to move freely along the bar to either side of the front of the wearer's rib cage, thus accommodating a wide variety of holding positions of the child. The portion of the flanged attachment that engages the bar can be shaped to also partially rotate about the bar allowing the wearer additional freedom of movement.

In a further embodiment, the hand/wrist support assembly includes a hand grip with either an integral or attached hand support. The hand/wrist support assembly is movable along the rigid bar.

DRAWINGS

FIGS. 20A and 20B illustrates harness strap portions of FIG. 14.

FIGS. 23A-23H show embodiments of the rigid bar in cross sectional view.

DESCRIPTION

The following terms are defined here for clarity and convenience. The term child is used collectively to mean infant, baby, toddler, or young child. Child carrier is an equivalent term for a child carrying device or a child carrying apparatus. The terms "first" and "second" are used to distinguish similar portions or parts of the described structure, however, they do not imply any particular order or preference. The use of the terms "left" or "right" in the description that follows refer to the left and right side from the wearer's perspective as depicted in drawings. Similarly, the terms "up" and "down" that follow refer to the orientation of various elements in relation to the orientation of the wearer's body. These terms are meant to aid in understanding the drawings and not meant to limit the claimed invention to a particular number or order of parts, a particular side of the wearer, or a particular direction. In addition, the term lateral, for the purposes of this disclosure, means tending toward one side of the wearer's body. For the purpose of this disclosure, a hand/wrist support assembly refers to a support assembly for supporting a hand, wrist, or upper forearm, or for supporting the combination of a hand and a wrist, the combination of a wrist and a upper forearm, or the combination of a hand, a wrist, and an upper forearm. The hand/wrist support assembly can be a hand/wrist sling assembly, as defined below, but is not limited to such. For the purpose of this disclosure, a hand/wrist sling assembly refers to a sling assembly for supporting a hand, wrist, or upper forearm, or for supporting the combination of a hand and a wrist, the combination of a wrist and a upper forearm, or the combination of a hand, a wrist, and an upper forearm. For the purpose of this disclosure, a "dual-shoulder harness" is used to collectively describe a strapped harness, that when worn is supported by both shoulders of the wearer and is configured as a restrained support.

Figure 1:
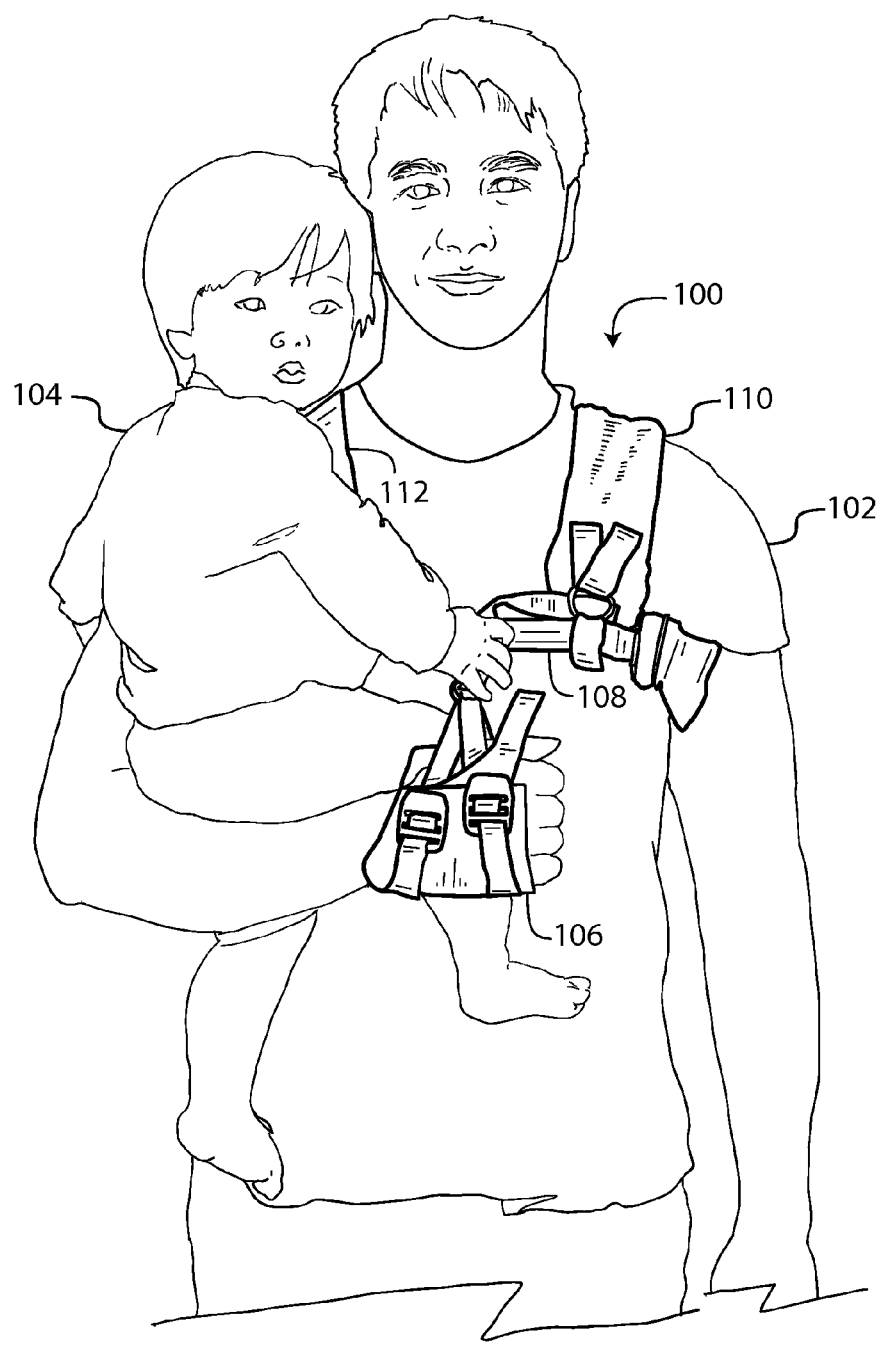
FIG. 1 illustrates a front view of an embodiment of a child carrier supporting a child with the wearer's right arm. The hand/wrist sling assembly is positioned approximately midway along a rigid bar.
Figure 2:
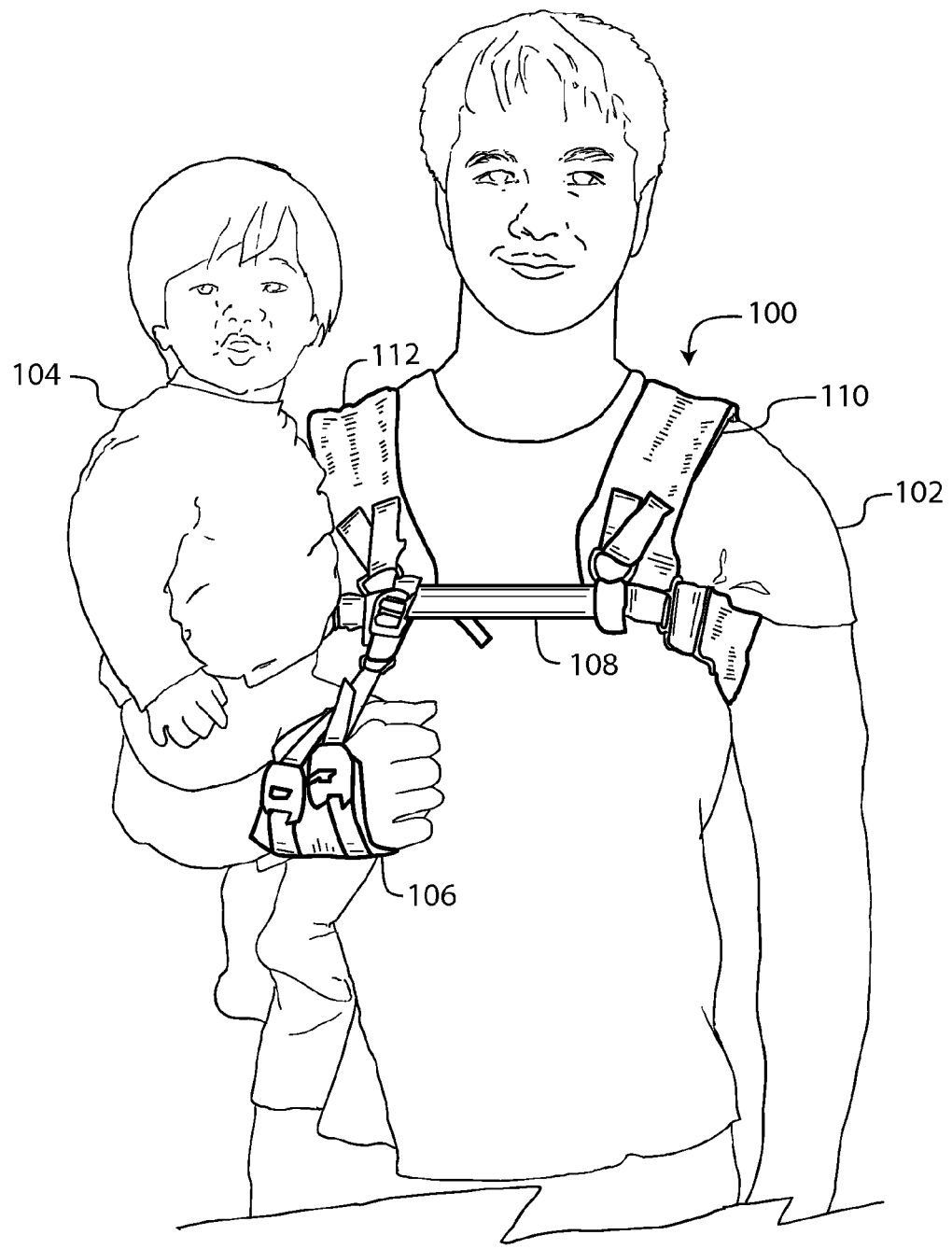
FIG. 2 illustrates a front view of the child carrier of FIG. 1 shown supporting the child with the wearer's right arm. The hand/wrist sling assembly is positioned toward the right along the rigid bar.
Figure 3:
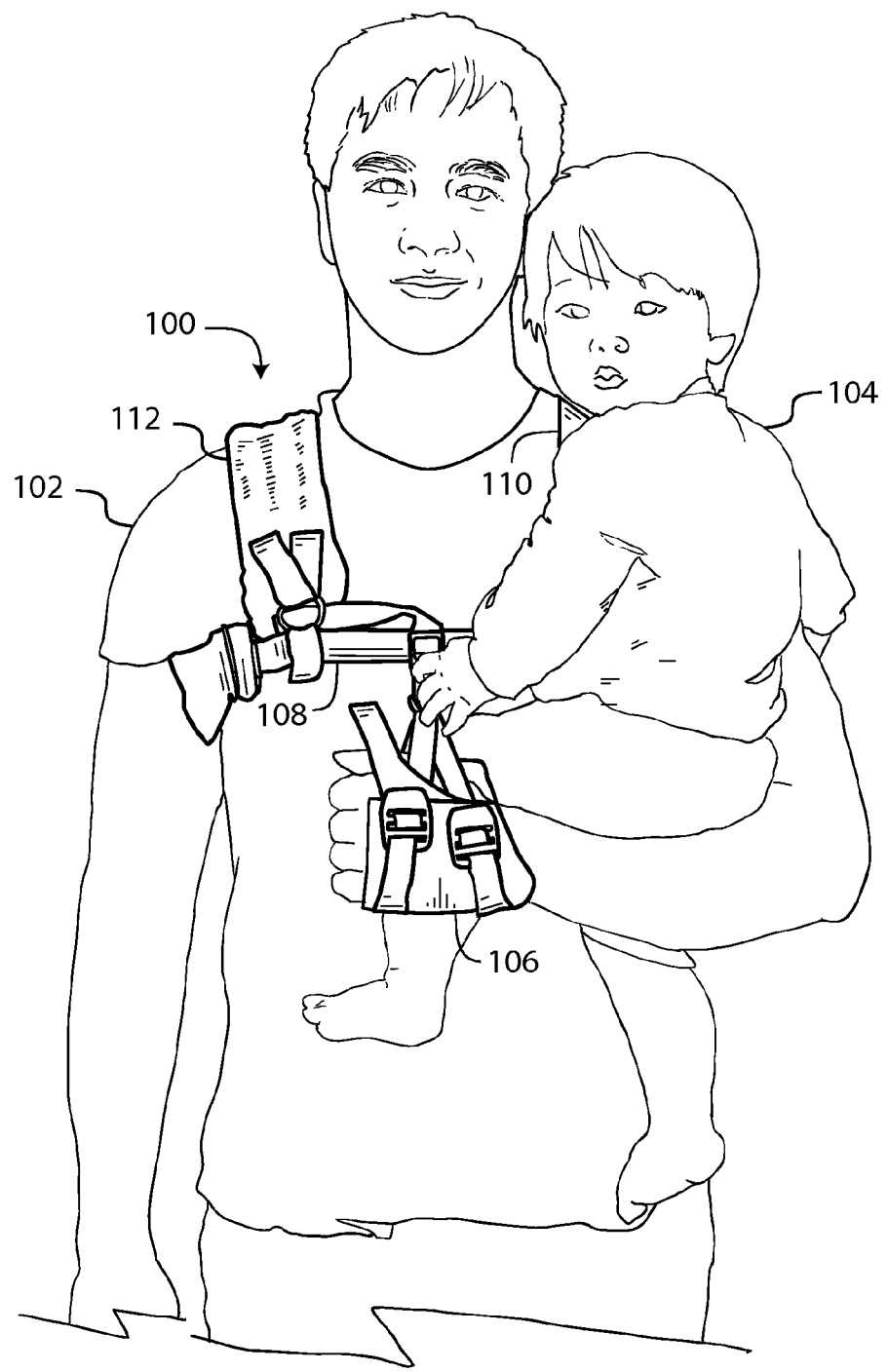
FIG. 3 illustrates a front view of the child carrier of FIG. 1 shown supporting the child with the wearer's left arm.

The description that follows is made with reference to figures, where like numerals refer to like elements throughout the several views. FIGS. 1, 2, and 3 illustrate an embodiment of a child carrier 100 shown worn by a wearer 102 holding a child 104. The child carrier 100 includes a hand/wrist support assembly in the form of a hand/wrist sling assembly 106. The hand/wrist sling assembly 106 is slidable along and rotatable about a rigid bar 108. The rigid bar 108 is held transversely at the front of the wearer's rib cage between and by a first shoulder strap portion 110 and a second shoulder strap portion 112. The rigid bar 108 holds the first shoulder strap portion 110 and the second shoulder strap portion 112 apart, at a position proximate to the end portions of the rigid bar 108. The first shoulder strap portion 110 and the second shoulder strap portion 112 form a portion of a dual-shoulder harness. The first shoulder strap portion 110 and the second shoulder strap portion 112 are attached to the top and side of a corresponding end of the rigid bar 108. The first shoulder strap portion 110 and the second shoulder strap portion 112 are illustrated as being substantially flat and cushioned. Alternatively, the first shoulder strap portion 110 and the second shoulder strap portion 112 can also be tubular or rounded, and either cushioned or not cushioned. Starting from the topside of rigid bar 108, the first shoulder strap portion 110 and the second shoulder strap portion 112 extends laterally over the front of the wearer's ribcage, over a shoulder, and under an arm corresponding to the shoulder and attaching to the side of the rigid bar 108 corresponding to the topside attachment.

The hand/wrist sling assembly 106 is shown in FIGS. 1, 2, and 3 facilitating the wearer 102 with holding the child 104 in various positions. In FIG. 1, the wearer 102 is shown supporting the child 104 with their right arm. The hand/wrist sling assembly 106 supports the wearer's right hand and wrist along the center position of the rigid bar 108. In FIG. 2, the child 104 is supported by the wearer's right arm, but with the hand/wrist sling assembly 106 slid over to the right most position of the rigid bar 108.

In FIG. 3, the wearer 102 is supporting the child 104 with their left arm. The hand/wrist sling assembly 106 supports the wearer's left hand and wrist along the center position of the rigid bar 108. Switching from a right arm to left arm holding position, and vice versa, does not require removal or disassembly of the child carrier 100 from the wearer 102. The wearer 102 can simply remove one hand from the hand/wrist sling assembly 106 and place the other hand into the hand/wrist sling assembly 106.

Throughout this disclosure, a strap is defined as a piece of pliant or flexible material suitable for holding, securing or binding. For example, straps and strap portions for the dual-shoulder harness or sling assembly can be made of nylon, polyester, polypropylene, cotton, leather, or hemp. These can be formed into flat, tubular, or rounded shapes. The straps can be solid, hollow or layered, and non-woven or woven. Hollow or layered straps can be filled with a cushioning material. These examples are not meant to limit the claimed invention, but are provided as examples of suitable materials or suitable fabrics. Those skilled in the art will readily recognize other equivalent materials or combination of materials of suitable strength, shape, and flexibility, for dual-shoulder strap harness and for a weight bearing sling assembly.

Figure 4:
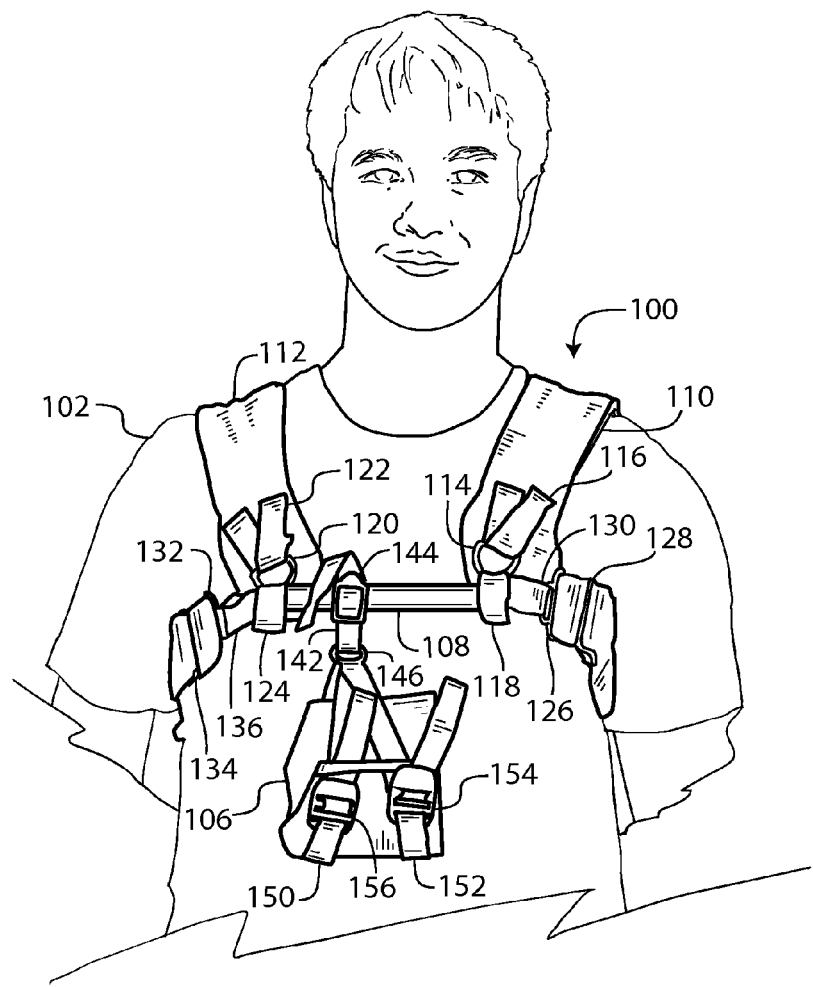
FIG. 4 illustrates a front view of the child carrier of FIG. 1 shown worn by the wearer without the child.
Figure 5:
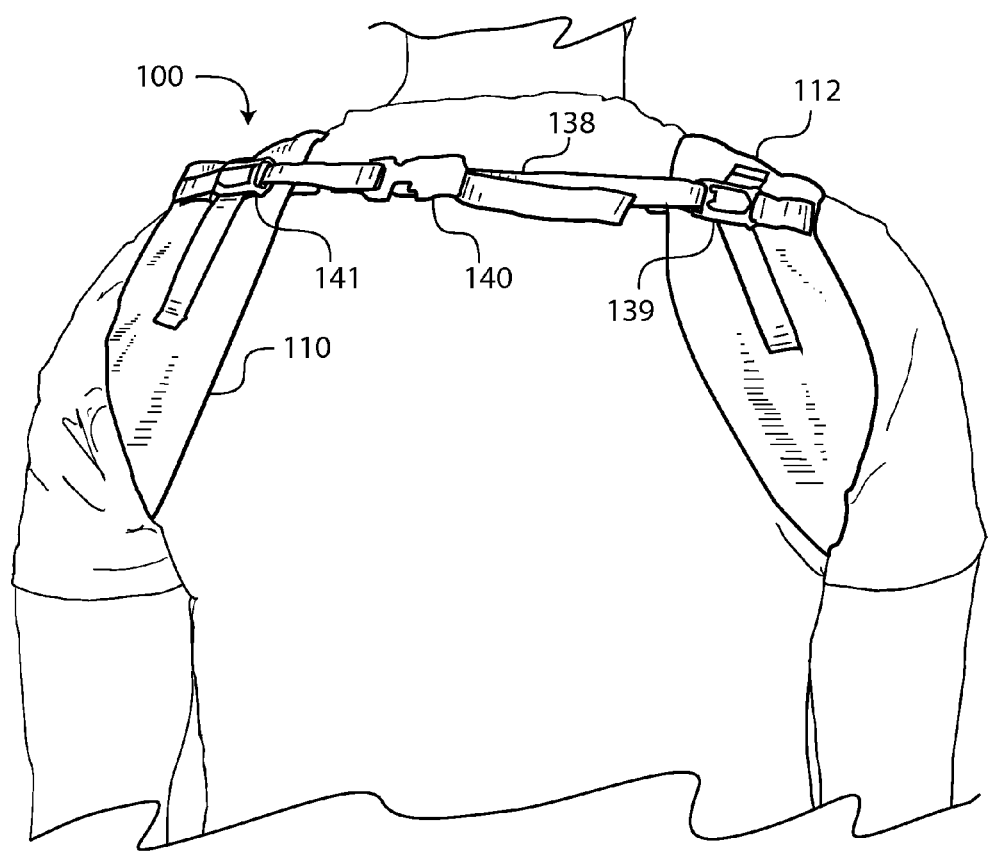
FIG. 5 illustrates a rear view of the child carrier of FIG. 1 shown worn by the wearer.
Figure 6:
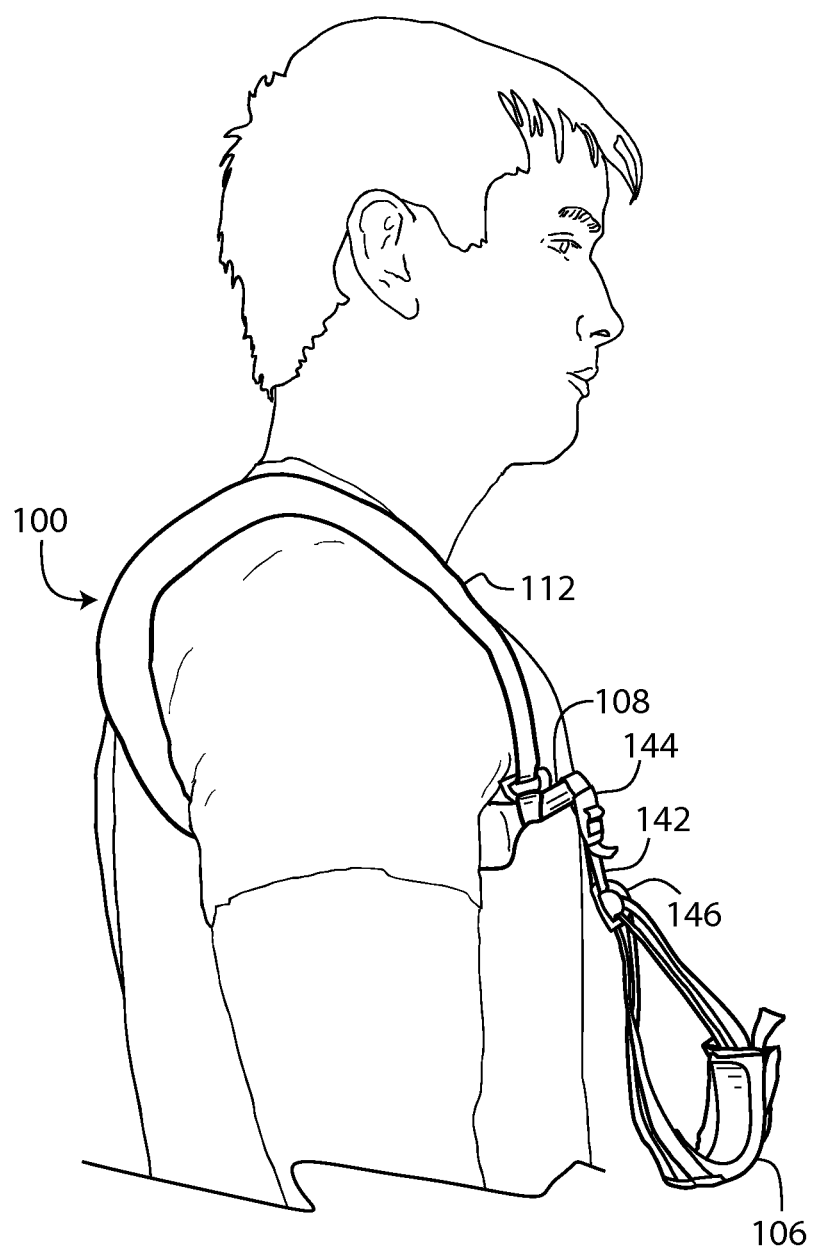
FIG. 6 illustrates a side view of the child carrier of FIG. 1 shown worn by the wearer.

For further clarity, FIGS. 4, 5, and 6, illustrate the child carrier 100 worn by a wearer 102 without the child 104 of FIGS. 1-3. Referring to FIGS. 4, 5, and 6, the rigid bar 108 of FIGS. 4 and 6 is supported between two frontal portions of the dual-shoulder harness. Each frontal portion is illustrated approximately lateral along the front of the wearer's body from the respective shoulder of the wearer. Specifically, the rigid bar 108 of FIGS. 4 and 6 is supported on the top and left side of the wearer 102 by the first shoulder strap portion 110. The first shoulder strap portion 110 is shown extending over the wearer's left shoulder and under their left arm. Similarly, the rigid bar 108 of FIGS. 4 and 6 is supported on the top and right side of the wearer 102 by the second shoulder strap portion 112. The second shoulder strap portion 112 is shown extending over the wearer's right shoulder and under their right arm. The rigid bar 108 can be covered with and enclosed by fabric or other material, for example, nylon, polypropylene, or polyester. A cushioning filler such as Ethylene vinyl acetate (EVA) foam, can optionally surround the bar within the fabric envelope.

FIG. 4 illustrates an example of how the first shoulder strap portion 110 and the second shoulder strap portion 112 of the dual-shoulder harness can be secured to the rigid bar 108. A first D-ring 114 secures a first end portion 116 of the first shoulder strap portion 110 to the rigid bar 108. The first end portion 116 can be sewn, heat bonded, glued, riveted, hook and loop fastened, or otherwise secured to itself to form the loop. The other end of the first D-ring 114 is secured to an attachment portion in the form of a first attachment loop 118 that extends upward from near the left end of the fabric covering of the rigid bar 108. A second D-ring 120, a second end portion 122, and a second attachment loop 124 similarly secure an end portion of the second shoulder strap portion 112 to rigid bar 108 near its right end. The first attachment loop 118 and the second attachment loop 124 can be made of a suitably strong material to support the weight of a child, for example, nylon, polyester, polypropylene, cotton, leather, or hemp. The first attachment loop 118 and the second attachment loop 124 can be secured to their respective shoulder strap portions by sewing, heat bonding, gluing, riveting, hook and loop fastening, or otherwise securing in a manner known to those skilled in the art.

Continuing to refer to FIG. 4, a second strap end portion of the first shoulder strap portion 110 goes under the wearer's left arm and is adjustably and removably secured to the left end of the rigid bar 108 through a first reducer loop 126 and a first single bar slide 128. The left end of the covering that surrounds the rigid bar 108 can be sewn, heat bonded, glued, riveted, hook and loop fastened, or otherwise secured to itself to form a first closed attachment loop 130 over the smaller end of the first reducer loop 126. Similarly, a second strap end portion of the second shoulder strap portion 112 goes under the wearer's right arm and is adjustably and removably secured to the right end of the rigid bar 108 through a second reducer loop 132 and a second single bar slide 134.

FIG. 5 illustrates a rear view the embodiment of FIG. 1 worn by the wearer 102. Referring to FIG. 5, a stabilizing back strap 138 is attached transversely between the first shoulder strap portion 110 and the second shoulder strap portion 112 and illustrated positioned between the wearer's shoulder blades. The stabilizing back strap 138 is slidable along an attachment to the first shoulder strap portion 110 and the second shoulder strap portion 112. Shown is a first adjustable slide 139 and a second adjustable slide 141, each shown secured to one of the end of the stabilizing back strap 138 in order to facilitate sliding of the stabilizing back strap 138. The first adjustable slide 139 and the second adjustable slide 141 illustrated are typically called sternum slides. The stabilizing back strap 138 is detachably attached in order to accommodate the wearer 102 putting on and removing the child carrier 100. In FIG. 5, a side release buckle 140 facilitates quick separation and attachment of the stabilizing back strap 138.

In FIGS. 4 and 6, the hand/wrist sling assembly 106 is held securely to the rigid bar 108 by a hanging strap 142. The hanging strap 142 is secured to the rigid bar 108 by looping a portion of a hanging strap 142 through double bar slide 144. The hanging strap 142 is secured to the hand/wrist sling assembly 106 by looping the hanging strap 142 through a D-ring 146 secured to the hand/wrist sling assembly 106. The double bar slide 144 facilitates independent adjustment of the length of the hanging strap 142 and the tightness of the strap loop around the rigid bar 108. The latter adjusts the tension or friction of sliding of the hand/wrist sling assembly 106 along the rigid bar 108. The hanging strap 142 is illustrated as a flat strap. Alternatively, the flat strap can be rounded or tubular, cushioned or not cushioned.

Figure 7:
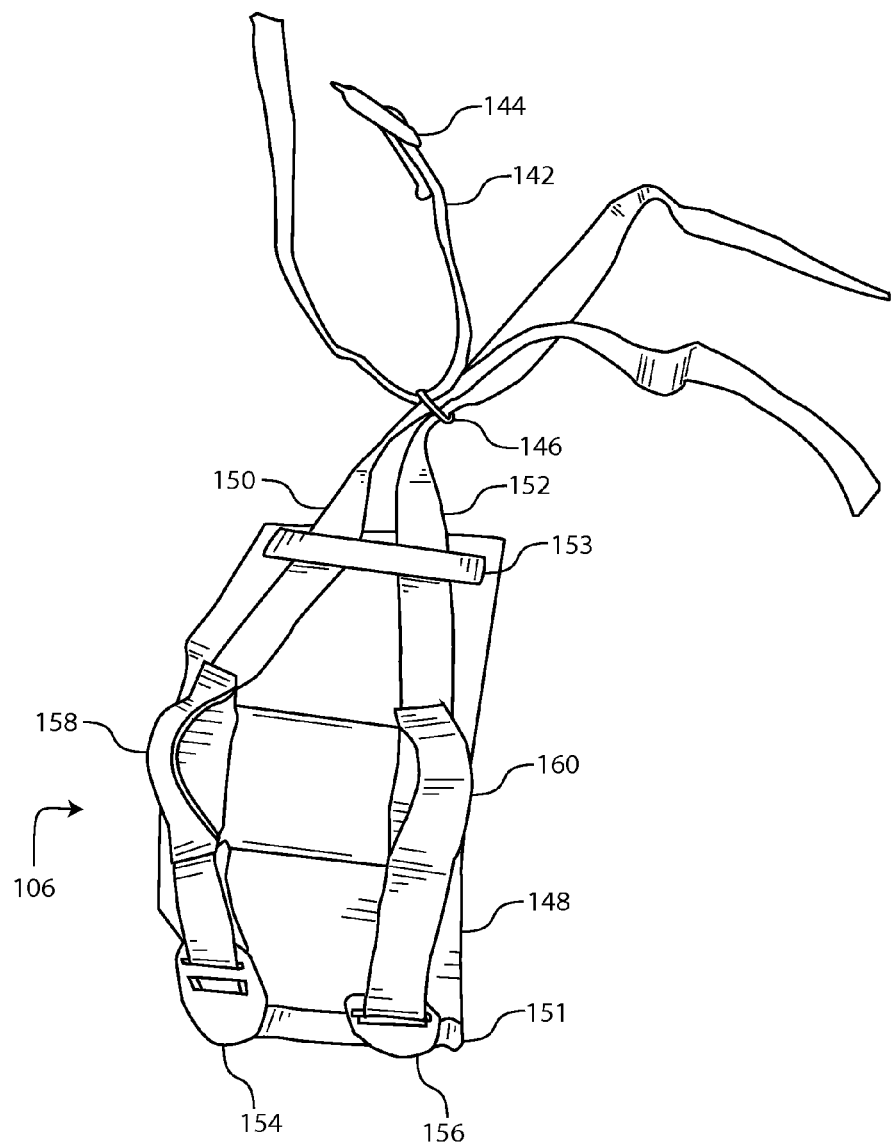
FIG. 7 illustrates the hand/wrist sling assembly of FIG. 1.

FIG. 7 shows the hand/wrist sling assembly 106, hanging strap 142, double bar slide 144, and D-ring 146. The hand/wrist sling assembly 106 includes a cushioned hand/wrist support 148. A first adjustment strap 150 and a second adjustment strap 152 facilitates adjusting the lateral angle of the cushioned hand/wrist support 148. The lateral angle is the angle along the supported limb of the wearer 102. In FIG. 7, the lateral angle is the angle between the hand and wrist of the cushioned hand/wrist support 148. The cushioned hand/wrist support 148 can be filled with a cushioning material such as cotton, polyester fiber, visco-elastic polyurethane foam, or ethylene-vinyl acetate (EVA) foam. Those skilled in the art will readily recognize other cushioning materials with equivalent properties. In the embodiment of FIG. 7, the first adjustment strap 150 and the second adjustment strap 152 are held in captive relation to cushioned hand/wrist support 148 by a first strap retainer 151 and a second strap retainer 153. The first strap retainer 151 and the second strap retainer 153 can be captive loops of fabric. The first strap retainer 151 and the second strap retainer 153 can be sewn, heat bonded, glued, riveted, hook and loop fastened, or otherwise secured to the cushioned hand/wrist support 148. The first adjustment strap 150 is secured to one bar portion of the first double bar slide 154. Referring to FIGS. 4 and 7, the other end of the first adjustment strap 150 is secured to the other bar portion of the first double bar slide 154. Similarly, the second adjustment strap 152 is secured to one bar portion of the second double bar slide 156 and the other end of the second adjustment strap 152 is secured to the other bar portion of the second double bar slide 156. A first gripping strap 158 is secured to the first adjustment strap 150 and a second gripping strap 160 is secured to the second adjustment strap 152. The first gripping strap 158 and the second gripping strap 160 help facilitate maneuvering and removal of the hand/wrist sling assembly 106 from the wearer's hand, wrist, or forearm with their free hand. While the first adjustment strap 150, the second adjustment strap 152, first gripping strap 158, and second gripping strap 160 are illustrated as flat straps, these straps can also be rounded or tubular, and cushioned or not cushioned.

Figure 8:
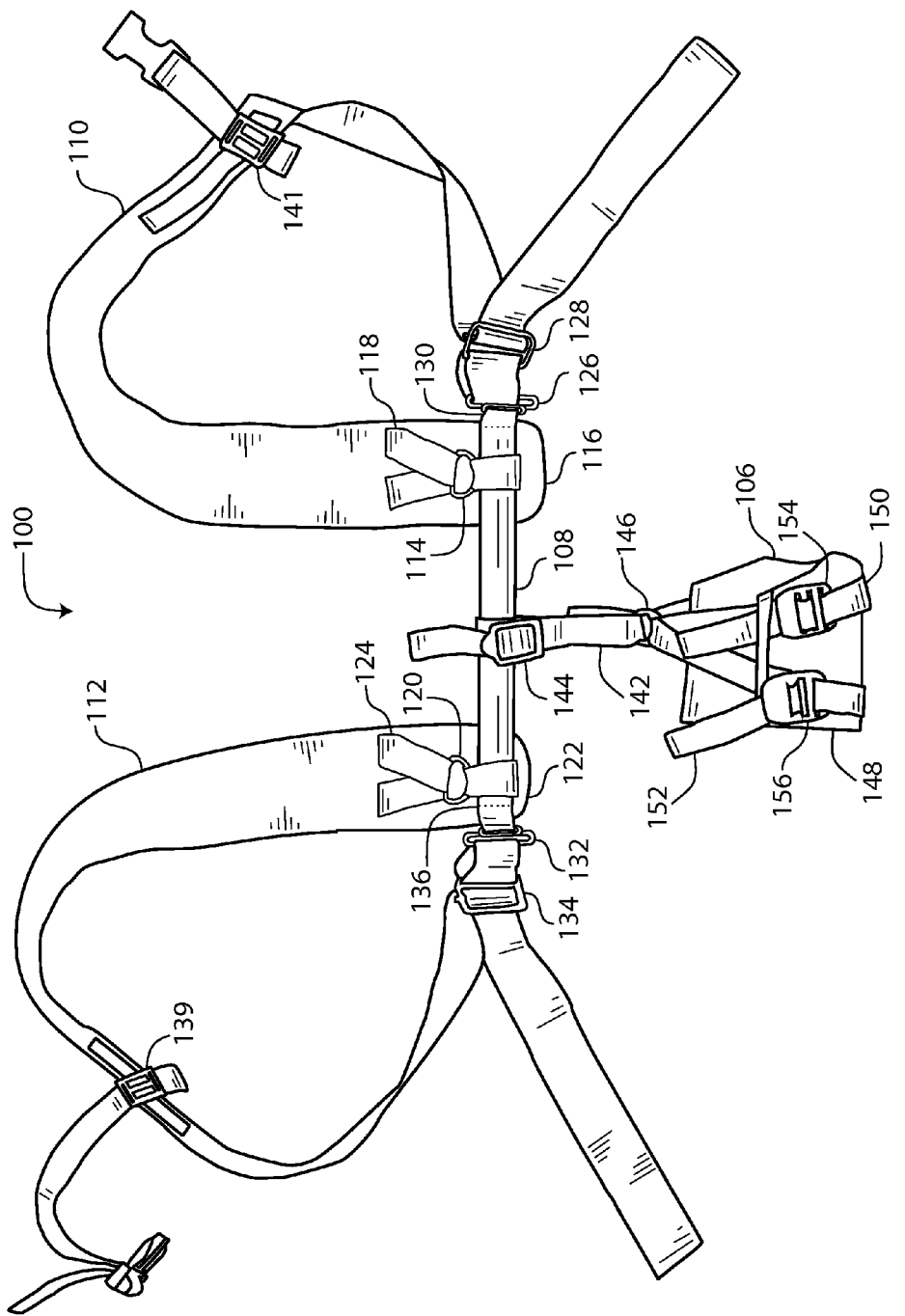
FIG. 8 illustrates an assembled view of the child carrier of FIG. 1.
Figure 9:
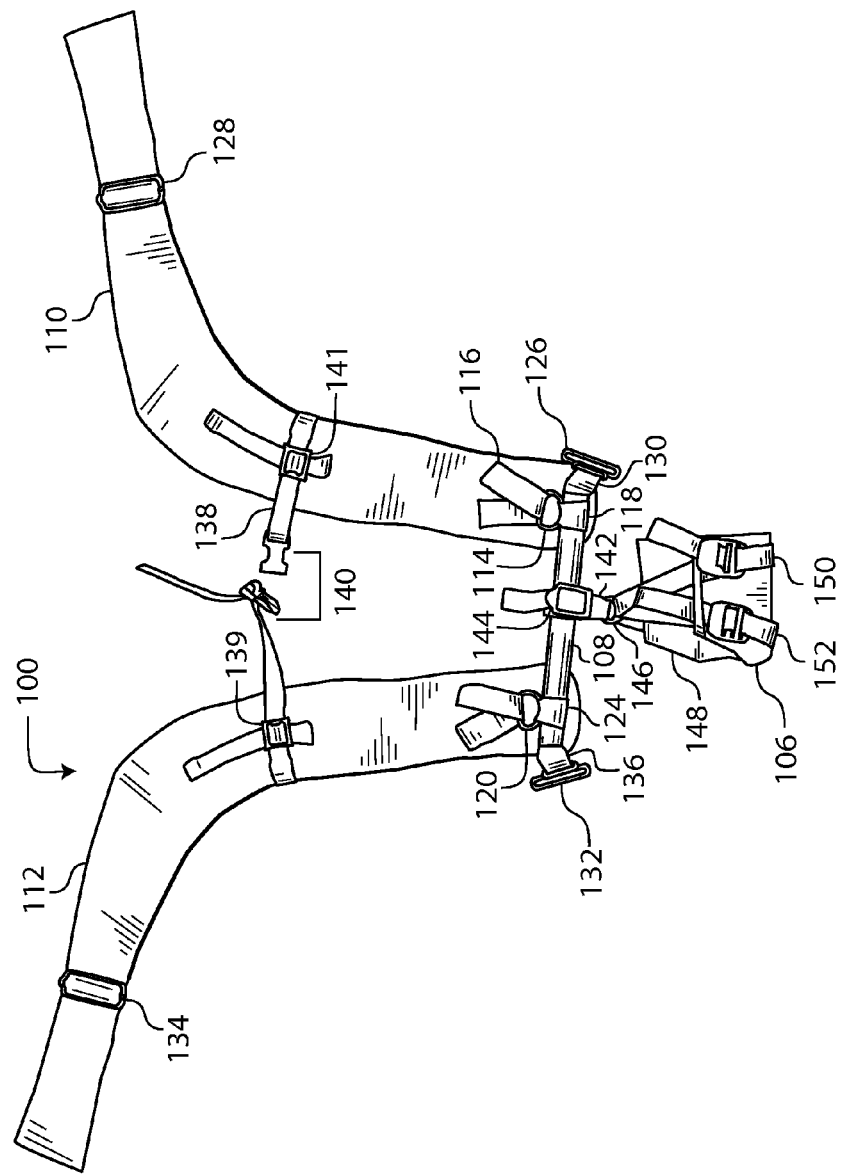
FIG. 9 illustrates a partially assembled view of FIG. 1.

FIG. 8 illustrates the child carrier 100 of FIG. 1 in fully assembled view. FIG. 9 illustrates the child carrier 100 of FIG. 1 with the strap ends of the first shoulder strap portion 110 and the second shoulder strap portion 112 disengaged from the first reducer loop 126 and the second reducer loop 132 for clarity. FIGS. 8 and 9 illustrate the various components in their previously defined relationships. Referring to FIGS. 8 and 9, these components include the hand/wrist sling assembly 106 with corresponding hanging strap 142, double bar slide 144, D-ring 146, cushioned hand/wrist support 148, the first adjustment strap 150 and the second adjustment strap 152, the first double bar slide 154 and the second double bar slide 156; the rigid bar 108 with corresponding first attachment loop 118 and second attachment loop 124, first closed attachment loop 130, and a second closed loop attachment; the dual-shoulder harness including the first shoulder strap portion 110 and the second shoulder strap portion 112 with corresponding first D-ring 114 and second D-ring 120, first end portion 116 of the first shoulder strap portion 110 and the second end portion 122 of the second shoulder strap portion 112, the first single bar slide 128 and the second single bar slide 134; and the stabilizing back strap 138 with side release buckle 140, the first adjustable slide 139, and the second adjustable slide 141. The first end portion 116 and the second end portion 122 are shown in FIG. 8 but not FIG. 9.

Figure 10:
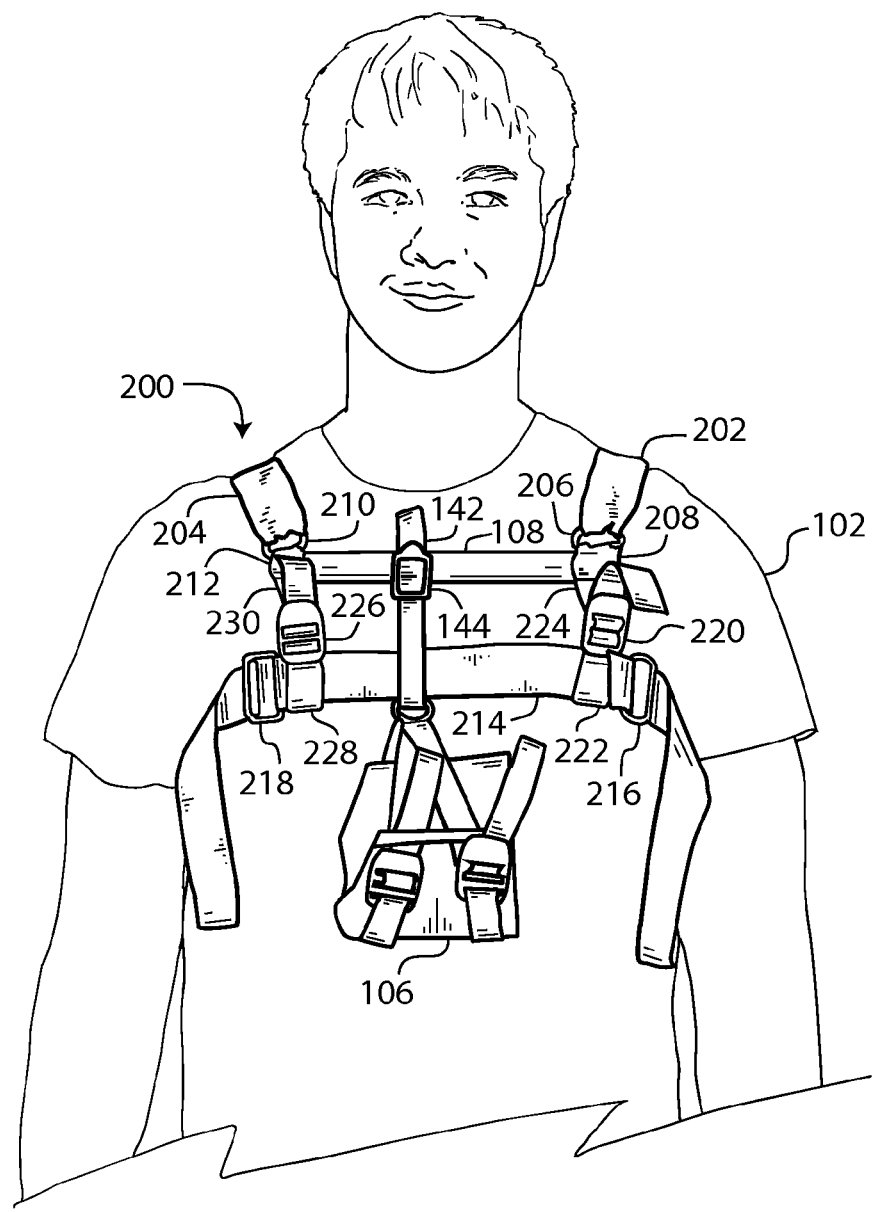
FIG. 10 illustrates a front view of another embodiment of a child carrier shown worn by the wearer.
Figure 11:
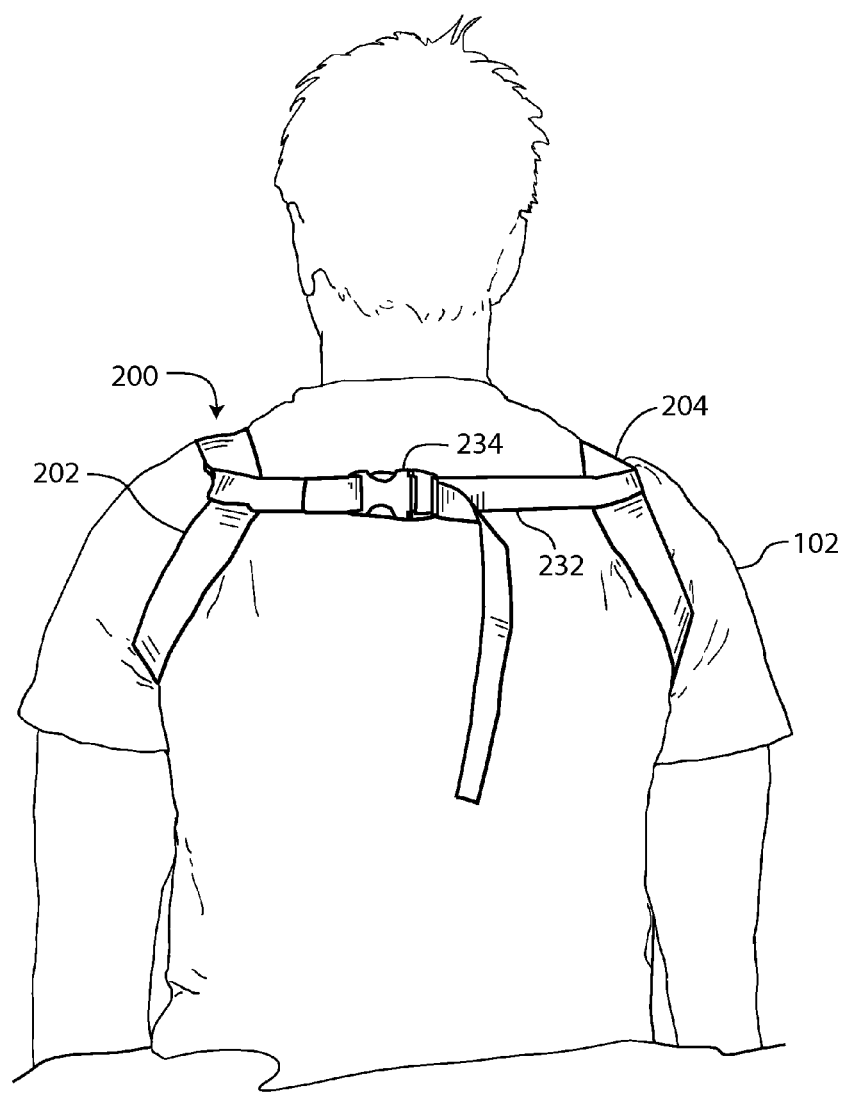
FIG. 11 illustrates a rear view of the child carrier of FIG. 10 shown worn by the wearer.
Figure 12:
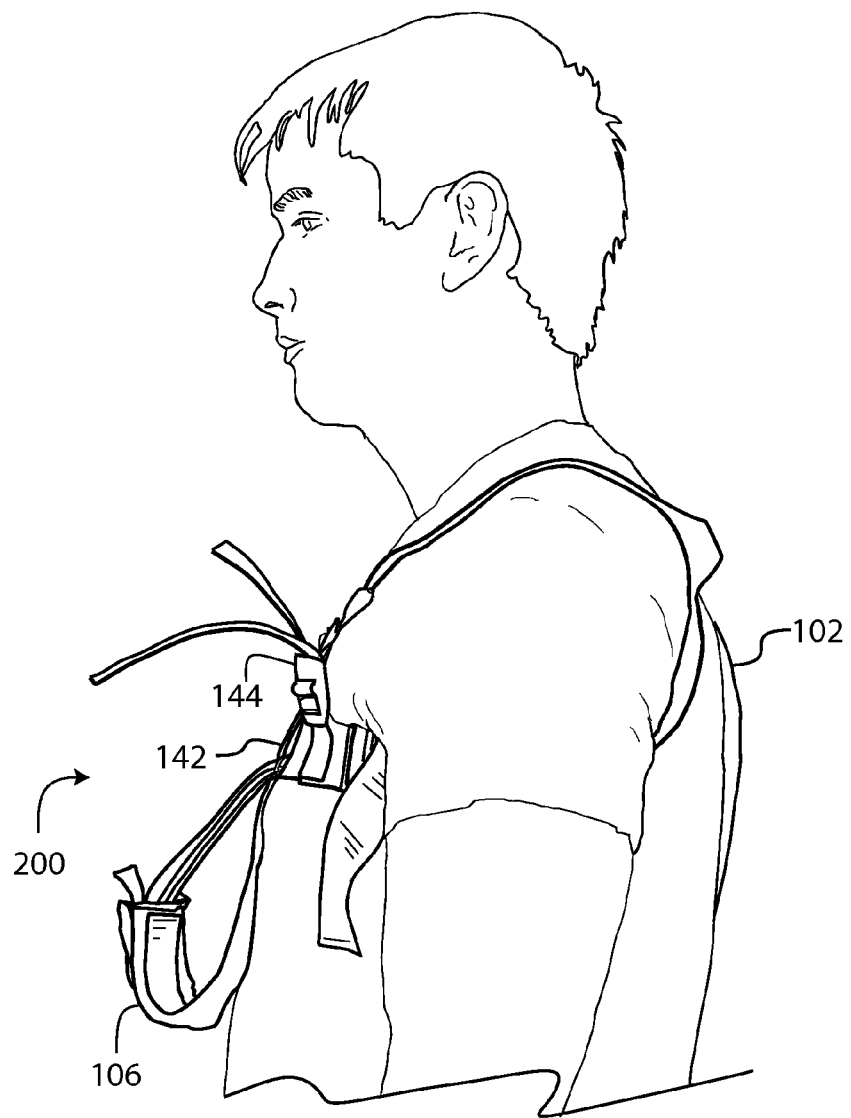
FIG. 12 illustrates a side view of the child carrier of FIG. 10 shown worn by the wearer.
Figure 13:
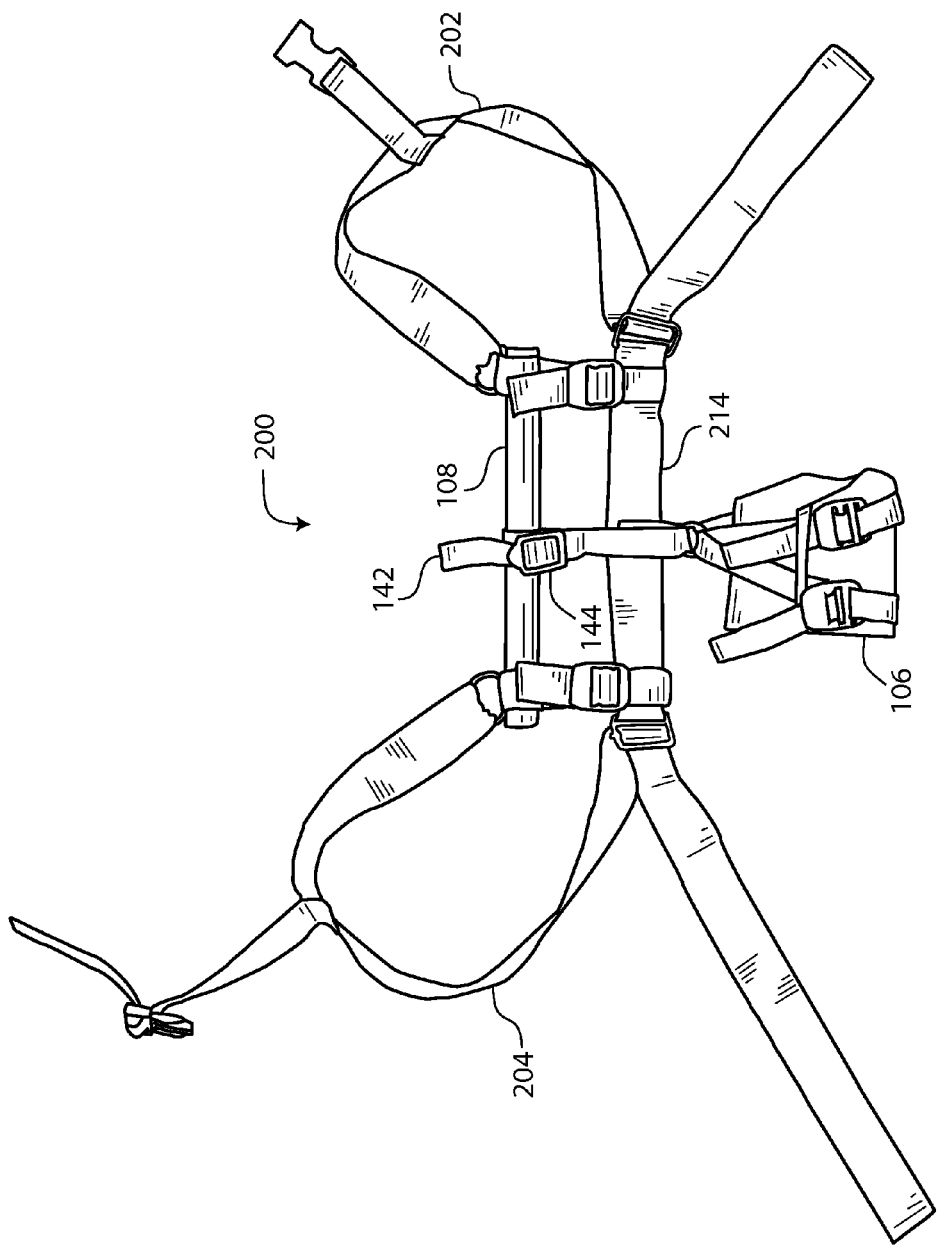
FIG. 13 illustrates an assembled view of the child carrier of FIG. 10.

FIGS. 10-13 illustrate a child carrier 200. In FIGS. 10-12, the child carrier 200 is shown worn by a wearer 102. Referring to FIGS. 10, 12, and 13, the child carrier 200 incorporates the hand/wrist sling assembly 106, hanging strap 142, double bar slide 144, and rigid bar 108 in cooperative relation as previously described, with the hand/wrist sling assembly 106 slidable along and rotatable about the rigid bar 108.

Referring to FIG. 10, the rigid bar 108 is held transversely at the front of the wearer's rib cage between and by a first shoulder strap portion 202 and a second shoulder strap portion 204. The rigid bar 108 holds the first shoulder strap portion 202 and the second shoulder strap portion 204 apart, at a position proximate to the end portions of the rigid bar 108. The first shoulder strap portion 202 and the second shoulder strap portion 204 form a portion of a dual-shoulder strap harness. A fabric sleeve covers the rigid bar 108. The first shoulder strap portion 202 is secured to rigid bar 108 by a D-ring 206 and the first attachment loop 208 above the left end portion of the rigid bar 108. Similarly, the second shoulder strap portion 204 is secured to the rigid bar 108 by a D-ring 210 and the second attachment loop 212 above the right end portion of the rigid bar 108. The first attachment loop 208 and the second attachment loop 212 can be formed from materials and secured by means similar to those described for the first attachment loop 118 and the second attachment loop 124 of FIG. 4.

Referring to FIGS. 10 and 11, the first shoulder strap portion 202 extends over the wearer's left shoulder and under their left arm. Similarly, the second shoulder strap portion 204 extends over the wearer's right shoulder and under their right arm. Referring to FIG. 10, the ends of the first shoulder strap portion 202 and the second shoulder strap portion 204 that looped under the arms are secured together by a transverse strap 214 positioned below the rigid bar 108 and across the front of the wearer's rib cage. The transverse strap 214 is shown secured to each side of shoulder strap portions ends by a first bar slide 216 and a second bar slide 218.

Continuing to refer to FIG. 10, the left side of the rigid bar 108 is secured to the left side of the transverse strap 214 by a double bar slide 220. The double bar slide 220 connects a strap portion 222 projecting upwardly away from the left side of the transverse strap 214 and a hanging harness strap 224 projecting downward from the fabric cover of the rigid bar 108. Similarly the right side of the rigid bar 108 is secured to the right side of the transverse strap 214 by a double bar slide 226. The double bar slide 226 connects a strap portion 228 projecting upwardly away from the right side of the transverse strap 214 and a hanging harness strap 230 projecting downward from the fabric cover of the rigid bar 108.

Referring to FIG. 11, a stabilizing back strap 232 is secured transversely between the first shoulder strap portion 202 and the second shoulder strap portion 204 on the back of the wearer 102. The stabilizing back strap 232 is detachably attached in order to accommodate the wearer 102 putting on and removing the child carrier 200. The stabilizing back strap 232 is shown detachably attached by a side release buckle 234.

FIG. 13 shows a laid out view of the child carrier 200 for clarity. FIG. 13 shows the first shoulder strap portion 202, second shoulder strap portion 204, and transverse strap 214 in cooperation with the rigid bar 108.

Figure 14:
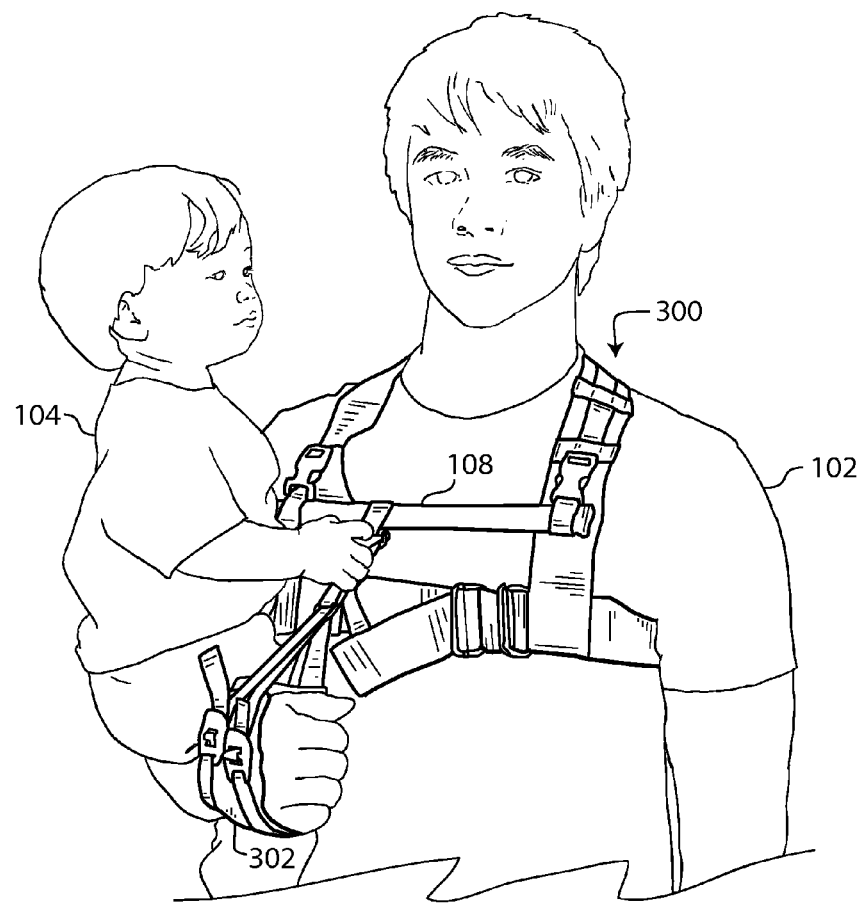
FIG. 14 illustrates a front view of another embodiment of a child carrier shown supporting a child with the wearer's right arm. The hand/wrist sling assembly is positioned toward the right along the rigid bar.
Figure 15:
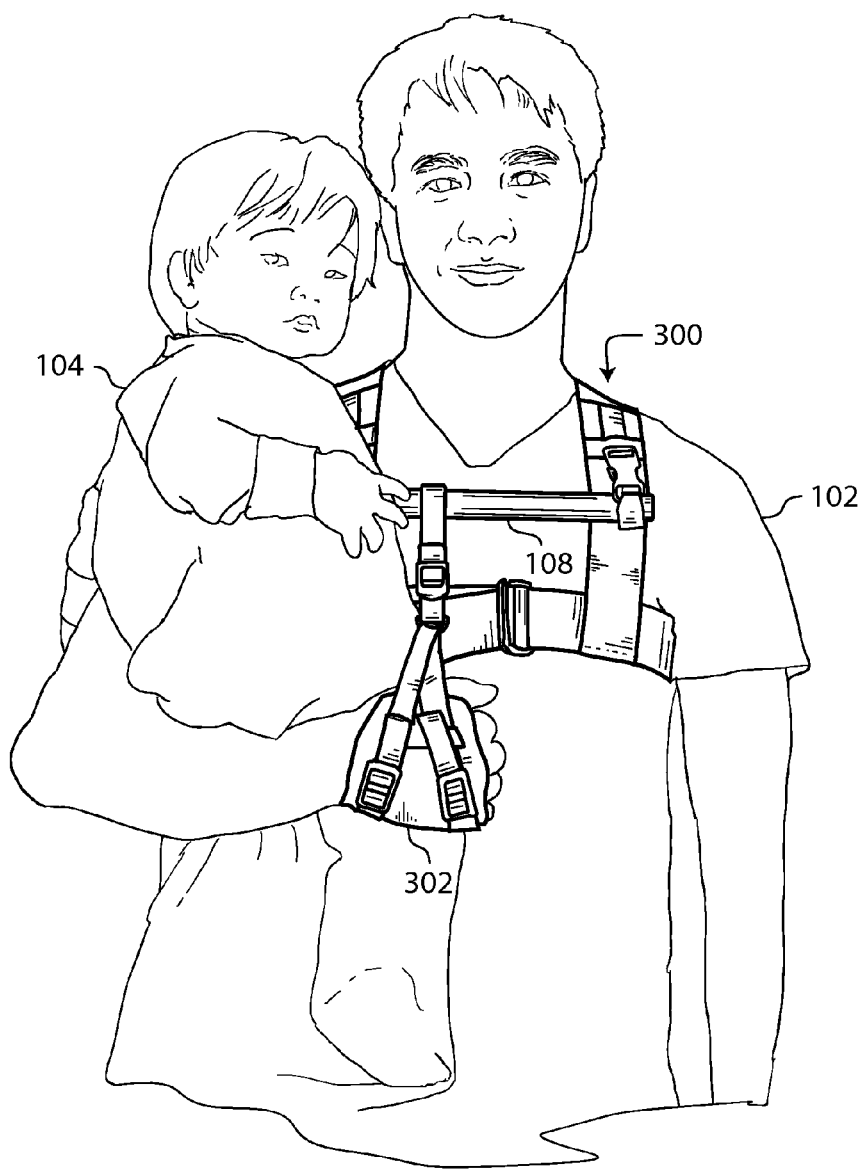
FIG. 15 illustrates a front view of the child carrier of FIG. 14 supporting a child with the wearer's right arm. The hand/wrist sling assembly is positioned approximately to the right of center along a rigid bar.

FIGS. 14-22 illustrate a child carrier 300. Referring to FIGS. 14 and 15, the wearer 102 supports the child 104 in a similar manner as previously described using a hand/wrist support assembly in the form of a hand/wrist sling assembly 302. The hand/wrist sling assembly 302 is slidable along and rotatable about rigid bar 108. In both FIGS. 14 and 15, the wearer 102 is supporting the child 104 with their right arm with the assistance of the child carrier 300. In FIG. 14, the hand/wrist sling assembly 302 is positioned to the far right along the rigid bar 108. In FIG. 15, the hand/wrist sling assembly 302 is positioned approximately right of center along the rigid bar 108.

Figure 16:
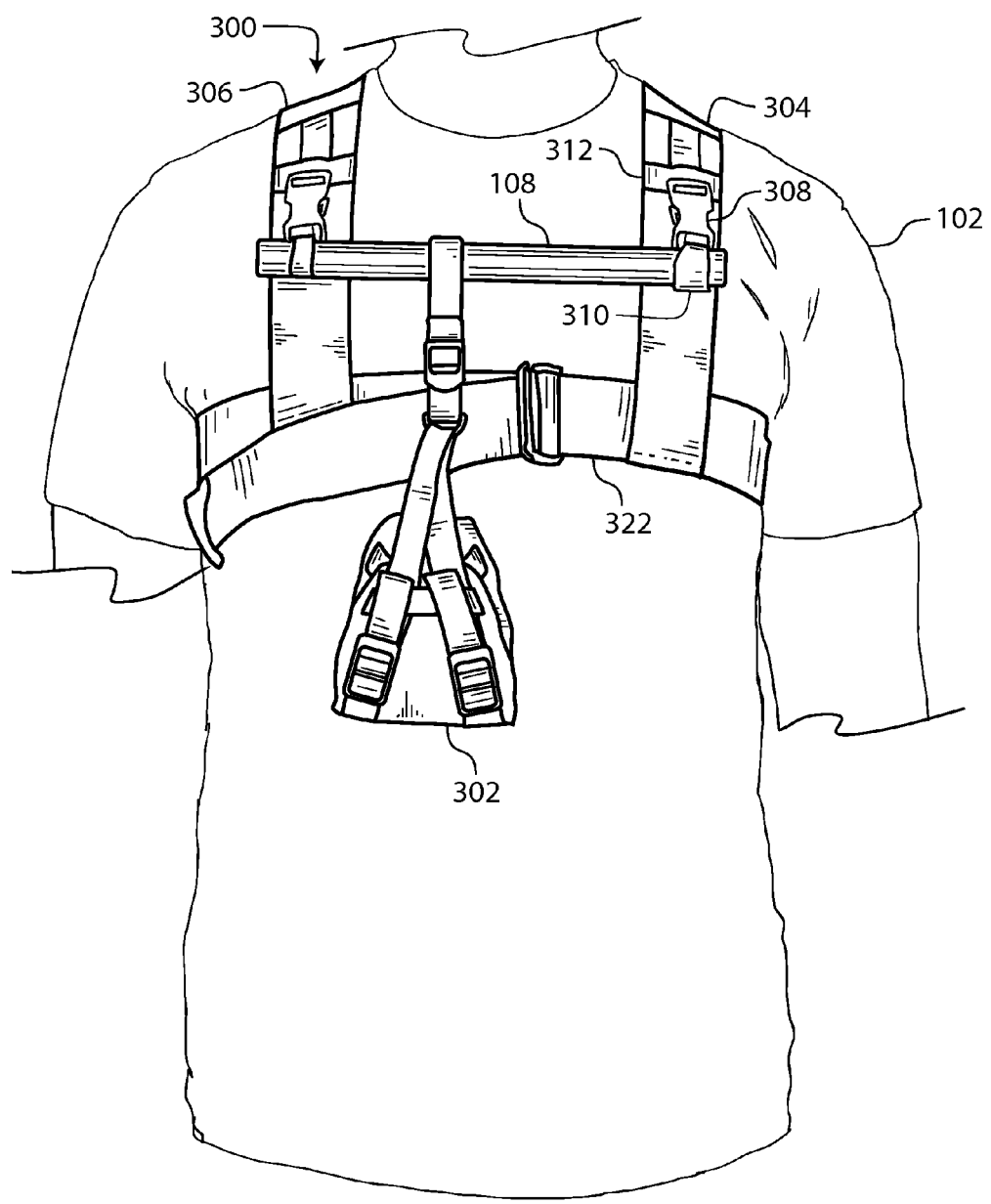
FIG. 16 illustrates a front view of the child carrier of FIG. 14 shown worn by a wearer without the child.
Figure 17:
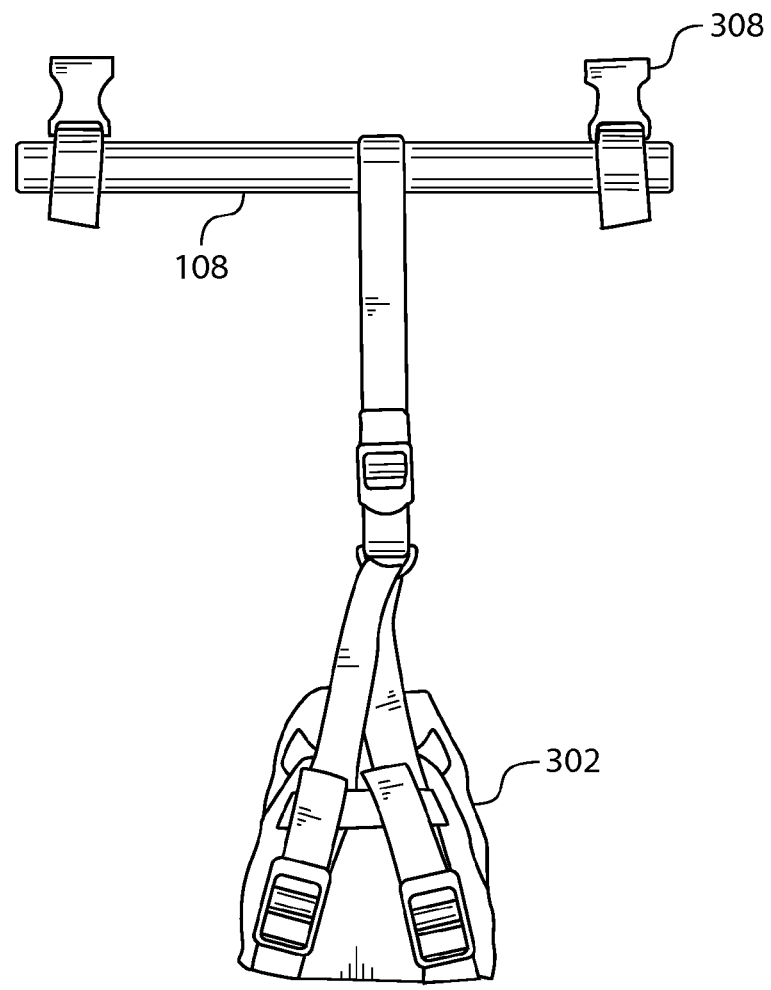
FIG. 17 illustrates a rigid bar and slidable hand/wrist sling assembly of FIG. 14.

For clarity, FIG. 16 illustrates the child carrier 300 worn by the wearer 102 without the child 104 of FIG. 15. Illustrated is the rigid bar 108, the hand/wrist sling assembly 302 in slidable connection with the rigid bar 108, and a dual-shoulder harness that includes a first shoulder strap portion 304, and a second shoulder strap portion 306. The rigid bar 108 is disposed transversely between the first shoulder strap portion 304 and the second shoulder strap portion 306 and secured thereto. The rigid bar 108 holds the first shoulder strap portion 304 and the second shoulder strap portion 306 apart, at a position proximate to the end portions of the rigid bar 108. The rigid bar 108 is removably secured on one end to the first shoulder strap portion 304 and on the other end to the second shoulder strap portion 306. Side release buckles 308 can be used, as illustrated, to removably connect the rigid bar 108 to first shoulder strap portion 304 and the second shoulder strap portion 306. A fabric cover can surround the rigid bar 108. One side of the side release buckle 308 can be secured to the rigid bar 108 by an attachment portion in the form of an attachment loop 310. The attachment loop 310 can be sewn, glued, riveted, or otherwise secured to the fabric cover surrounding the rigid bar 108. The other side of the side release buckle 308 can similarly be adjustably secured to one of the shoulder strap portions, as shown. FIG. 17 shows the rigid bar 108 and hand/wrist sling assembly 302 detached from the shoulder harness and showing the female half of each of the side release buckles 308.

Figure 18:
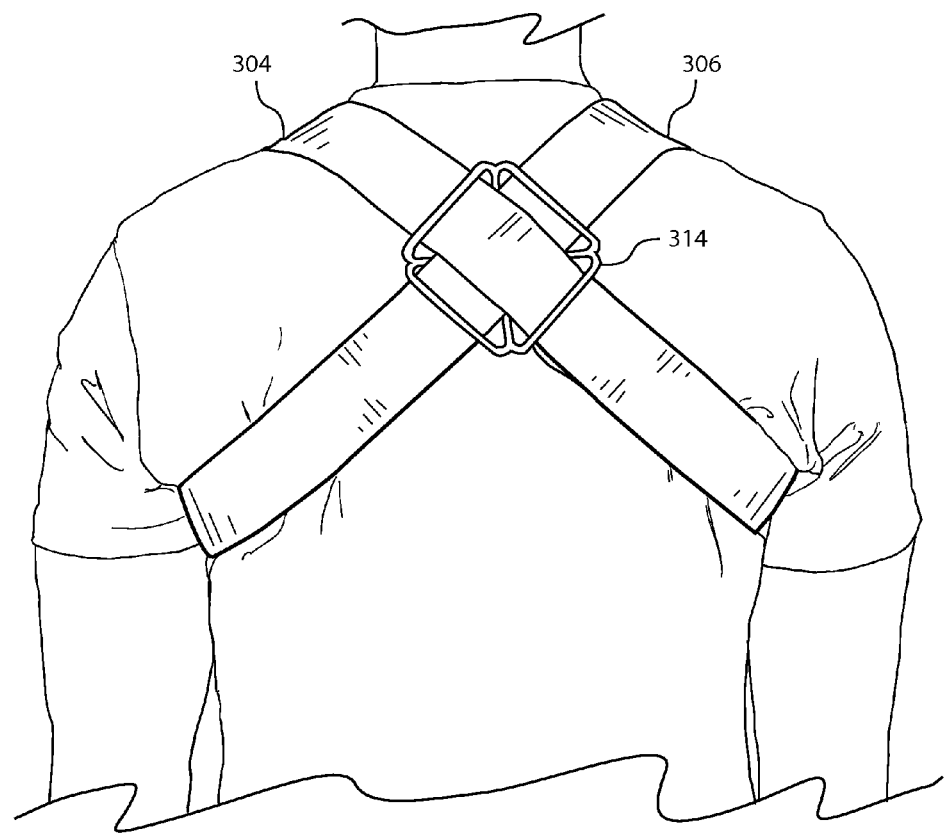
FIG. 18 illustrates a rear view of the child carrier of FIG. 14 shown worn by a wearer.

Referring to FIG. 18, the first shoulder strap portion 304 and the second shoulder strap portion 306 are cross-strapped through a four-way lash 314. Alternatively, the straps may be divided, looped and cross-strapped using an O-ring, fabric patch, or any other appropriate cross-strap coupling known to those skilled in the art. As a further alternative, the first shoulder strap portion 304 and the second shoulder strap portion 306 can be sewn, heat bonded, glued, riveted, hook and loop fastened, or otherwise secured at the where they either meet or cross.

Figure 19:
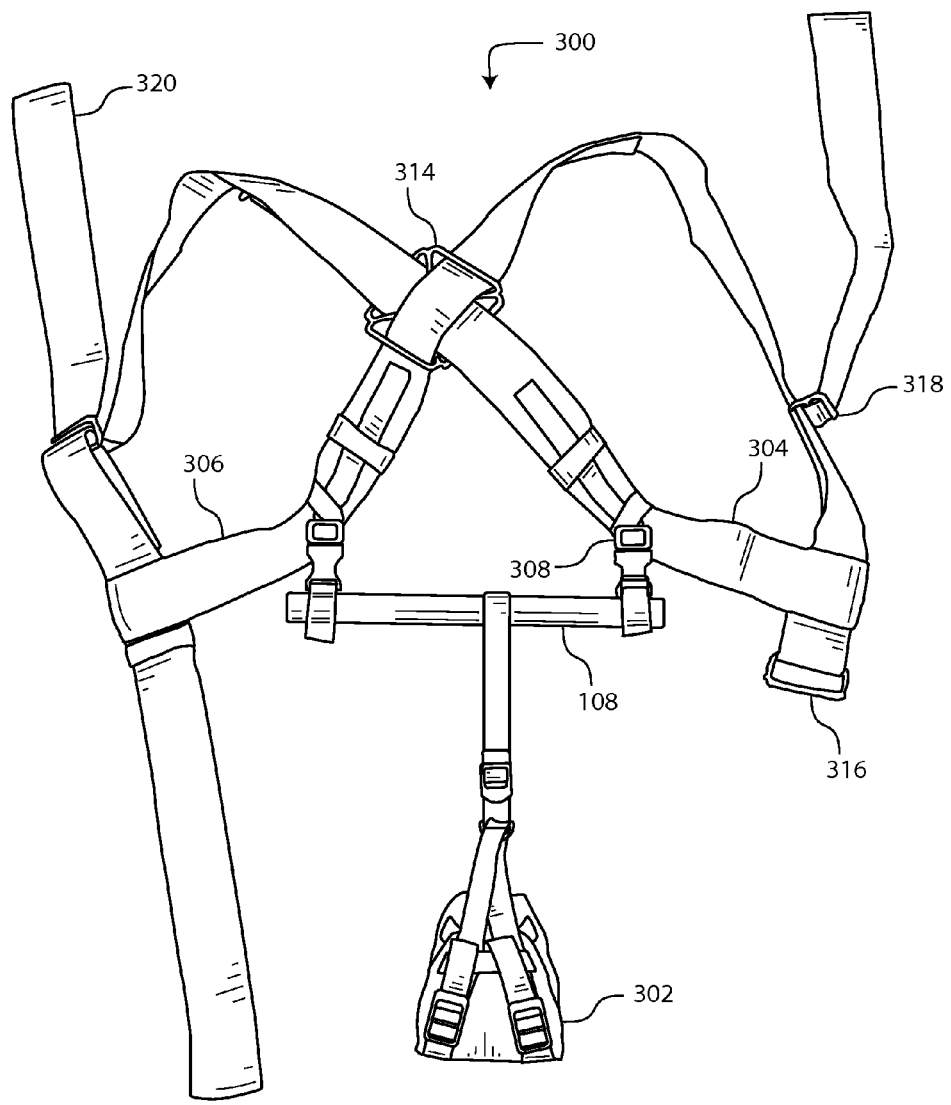
FIG. 19 illustrates an assembled view of the child carrier of FIG. 14.

FIG. 19 illustrates an assembled view of the child carrier 300, without the wearer 102 of FIG. 16, including the hand/wrist sling assembly 302, the rigid bar 108, the first shoulder strap portion 304, the second shoulder strap portion 306, the side release buckle 308, four-way lash 314, as well as a first bar slide 316, a second bar slide 318, and a third bar slide 320. The first bar slide 316, the second bar slide 318, and the third bar slide 320 are used to removably secure and adjust the length of the first shoulder strap portion 304 and the second shoulder strap portion 306. Note that although bar slides are shown, other strap or fabric connectors can be used to removably secure and adjust the length of the shoulder strap portions. For example, a slide release buckle with a ladder lock or a bar slide, cam buckle, or a slotted D-ring. Alternatively, a hook and loop fastener, such as sold under the brand name Velcro, or an equivalent, can be used in place of some or all of the bar slides.

FIGS. 20A and 20B show the first shoulder strap portion 304, the second shoulder strap portion 306, side release buckles 308, the first bar slide 316, and the four-way lash 314. The straps are illustrated as each having two portions secured at approximately right angles. Referring to FIG. 16, this configuration allows the formation of an adjustable transverse frontal strap portion 322 below the armpits of the wearer 102 approximately over the wearer's lower ribcage. The placement of the adjustable transverse frontal strap portion 322 depends on the size and shape of the wearer 102 in conjunction with individual strap adjustments.

Figure 21A:
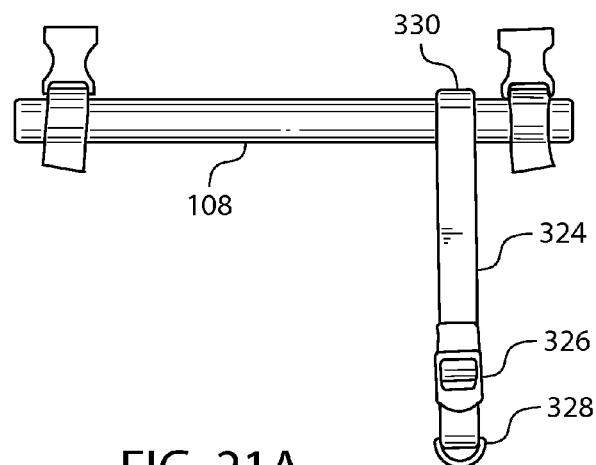
FIG. 21A illustrates the rigid bar and sliding strap portion of FIG. 14.
Figure 21B:
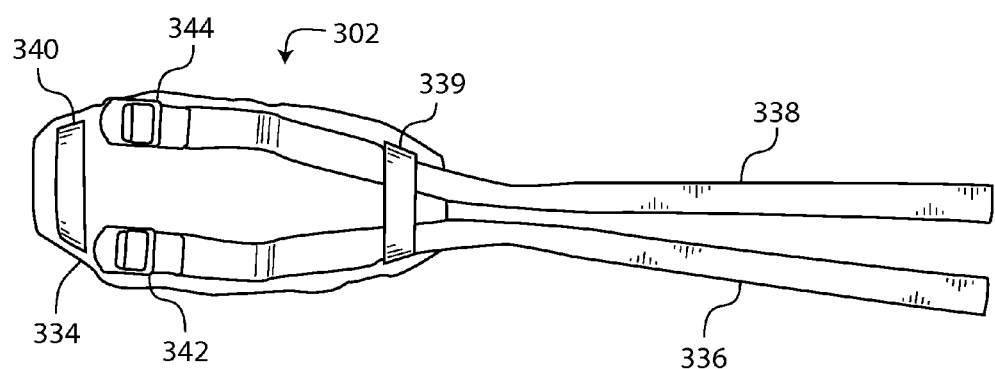
FIG. 21B illustrates the hand/wrist sling assembly portion of FIG. 14.

FIGS. 21A and 21B illustrate a partially assembled view of the rigid bar 108 and hand/wrist sling assembly 302 of FIG. 17. FIG. 21A shows a hanging strap 324, a bar slide 326, and D-ring 328. The hanging strap 324 includes a looped portion 330 that is looped over the rigid bar 108 and configured so that the hanging strap 324 is slidable along the length the rigid bar 108 and rotatable about the rigid bar 108. The looped portion 330 can be formed for example, by sewing, heat bonding, gluing, riveting, or otherwise securing the strap end to a portion of the hanging strap 324. Alternatively, the loop can be adjusted and made removable by looping the hanging strap 324 through a double bar slide as previously described.

FIG. 21B illustrates the hand/wrist sling assembly 302 laid flat to show the components. The hand/wrist sling assembly 302 includes a cushioned hand/wrist support 334. A first adjustment strap 336 and a second adjustment strap 338 to allow for adjustment of the lateral angle of the hand/wrist portion of the cushioned hand/wrist support 334. In the embodiment of FIG. 21B, the first adjustment strap 336 and the second adjustment strap 338 is held to cushioned hand/wrist support 334 by a first captive loop 339 and a second captive loop 340 at top and bottom ends of the cushioned hand/wrist support 334. The first adjustment strap 336 includes a looped end portion secured to a first double bar slide 342. Similarly, the second adjustment strap 338 includes a looped end portion secured to a second double bar slide 344. Referring to FIGS. 21A and 21B, the other end of the first adjustment strap 336 loops through D-ring 328 and is adjustably secured to a first double bar slide 342. Similarly, the other end of the second adjustment strap 338 loops through D-ring 328 and is adjustably secured to the second double bar slide 344.

Figure 22:
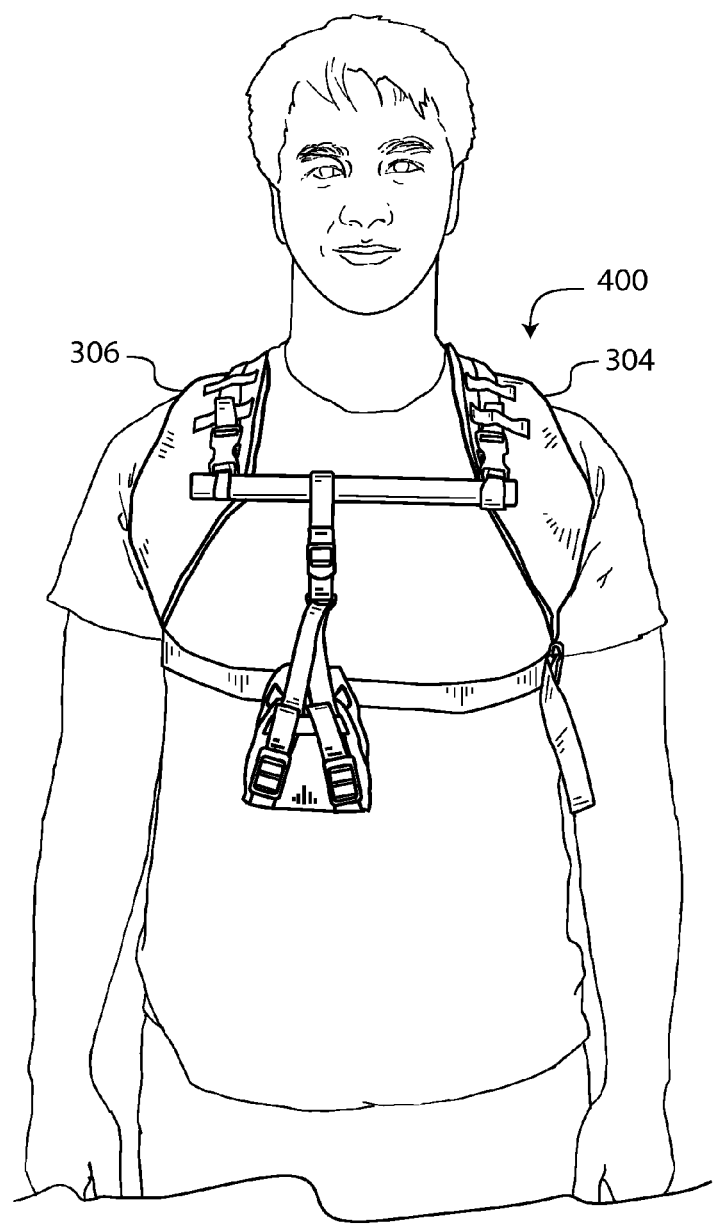
FIG. 22 illustrates a front view of another embodiment of a child carrier shown worn by a wearer.

FIG. 22 illustrates an embodiment substantially as described for FIGS. 14-21 where the first shoulder strap portion 304 and the second shoulder strap portion 306 have been widened and configured to accommodate additional cushioning. The first shoulder strap portion 304 and the second shoulder strap portion 306 as illustrated include a fabric shell surrounding a padding material. Typical padding materials include for example, cotton, polyester fiber, visco-elastic polyurethane foam, or EVA foam. Those skilled in the art will readily recognize other suitable padding materials.

FIGS. 23A-23H illustrate cross sectional views of alternative embodiments of the rigid bar 108. FIG. 23A shows a rigid bar 502 with a rectangular cross section and with a fabric covering 504, such as nylon, as previously described. Cushioning filler such EVA foam, can optionally surround the bar within the fabric envelope. FIG. 23B shows a hollow rigid bar 506 with a rectangular cross section. FIG. 23C shows a solid rigid bar 508 with a square cross section. FIG. 23D shows a hollow rigid bar 510 with a square cross section. FIG. 23E shows a solid rigid bar 512 with a circular cross section. FIG. 23F shows a hollow rigid bar 514 with a circular cross section. FIG. 23G shows a solid rigid bar 516 with an elliptical cross section. FIG. 23H shows a hollow rigid bar 518 with an elongated cross section. These embodiments of the rigid bar 108 are meant to be illustrative and not limiting. Other cross sections can be used, for example, to facilitate increased friction, or alternatively to control sliding, of the hand/wrist sling along the rigid bar 108. The rigid bar 108 illustrated in FIGS. 1-23 should be made of a material and thickness so that the rigid bar is strong enough substantially resist flexion or bending under the weight of a child. Suitable materials can include aluminum, titanium, steel, stainless steel, or carbon fiber. In addition, a rigid thermoplastic may make a suitable rigid bar, for example, a thermoplastic material such as polyoxymethylene (POM), sometimes sold under the brand name Delrin.

Figure 24A:
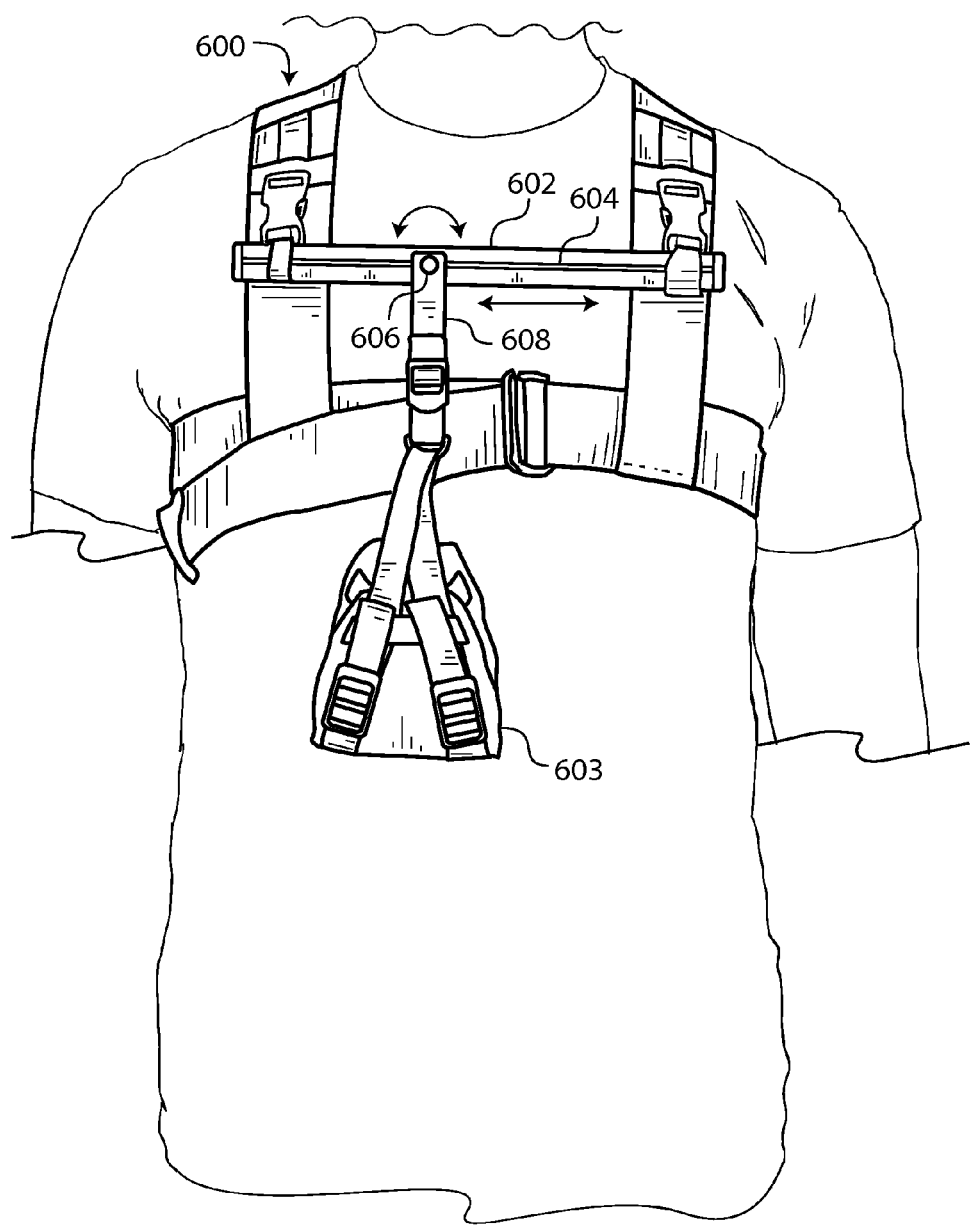
FIG. 24A illustrates a front view of an embodiment of a child carrier with a slotted rigid bar shown worn by a wearer.
Figure 24B:
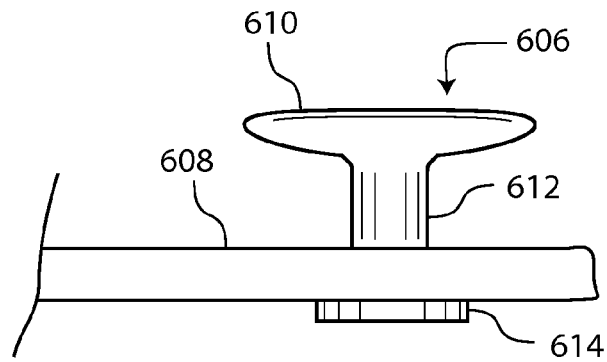
FIG. 24B illustrates a detailed view of a portion of the sliding strap of FIG. 24A.
Figure 24C:
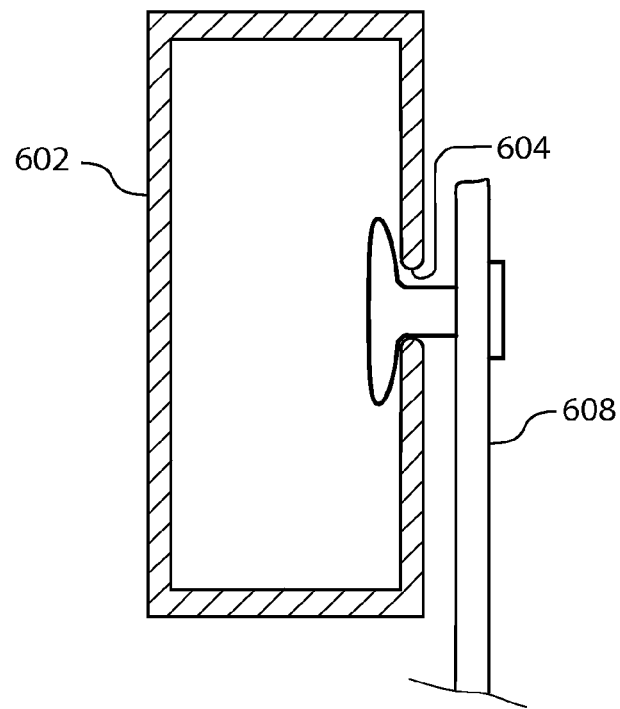
FIG. 24C illustrates the sliding strap engaged with the rigid bar of FIG. 24A. The rigid bar is in cross-sectional view.

FIG. 24A illustrates a child carrier 600 including a support harness substantially as described for FIGS. 16-21 with an alternative embodiment of a rigid bar 602 and alternative interface between the rigid bar 602 and a hand/wrist support assembly in the form of a hand/wrist sling assembly 603. The hand/wrist sling assembly 603, with the exception of the hanging strap attachment portion, is substantially as the hand/wrist sling assembly 106 described for FIG. 7. The rigid bar 602 of FIGS. 24A-C is hollow. The rigid bar 602 includes a slot 604 along its length. A flanged attachment 606, such as a flanged stud button, is attached to an end portion of the hanging strap 608, the hanging strap 608 engages the hand/wrist sling assembly 603. The flanged attachment 606 and hanging strap 608 are cooperatively configured so that the hand/wrist sling assembly 603 is slidable along the rigid bar 602.

FIG. 24B shows a detail side view of the end portion of the hanging strap 608. The flanged attachment 606, can be a stud button with a flanged portion 610, a shank 612, and a stud 614. The stud 614 and the shank 612 in combination hold the flanged attachment 606 to the hanging strap 608 of FIG. 24A. FIG. 24C illustrates a cross sectional end view of the rigid bar 602 engaged with the flanged attachment 606 and hanging strap 608. The flanged portion 610 is larger than the slot 604 but the shank 612 is smaller than the slot 604. This arrangement allows the flanged attachment 606 to captively slide along the length of the bar as well as rotate or swing as illustrated by arrows in FIG. 24A.

In one embodiment, the rigid bar 602 includes the slot 604 extending across the entire length of the rigid bar 602. The shank 612 of the flanged attachment 606 is slid into one end of the rigid bar 602. Referring to FIG. 24A, removable or permanently affixed end caps prevent the flanged attachment 606, and thus the hand/wrist sling assembly 603, from coming off the rigid bar 602. End caps can be removably or permanently affixed, for example, end caps can be plastic inserts, fabricated from hook and loop material. Alternatively, the end caps can be fabricated from a fabric that is secured to rigid bar 602, for example, by gluing, riveting, heat bonding. The rigid bar 602 can be detachably attached to the first shoulder strap portion 304 and the second shoulder strap portion 306 as previously described for FIGS. 16-21.

Figure 25:
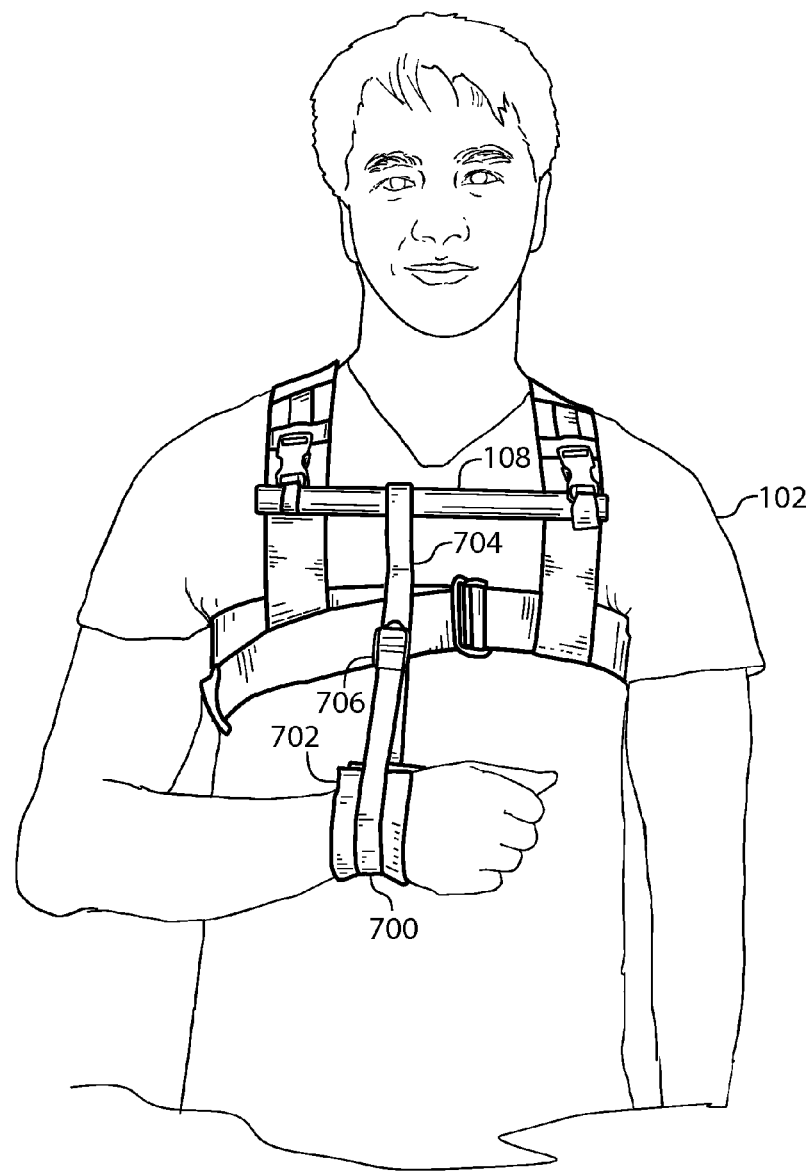
FIG. 25 illustrates an alternative hand/wrist sling assembly in combination with the harness assembly and the rigid bar of FIGS. 15-21 shown worn by the wearer.
Figure 26A:
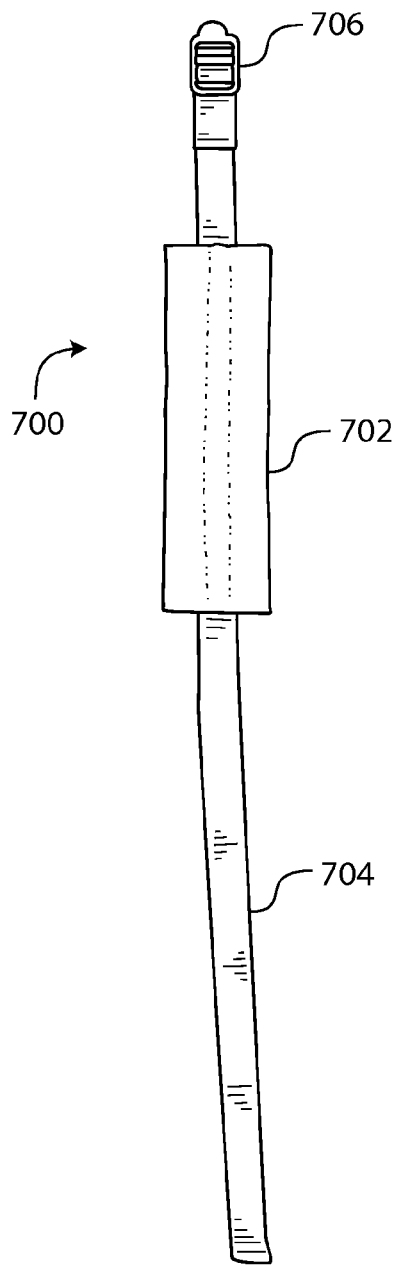
FIGS. 26A and 26B illustrates the front and back of the hand/wrist sling assembly 700.
Figure 26B:
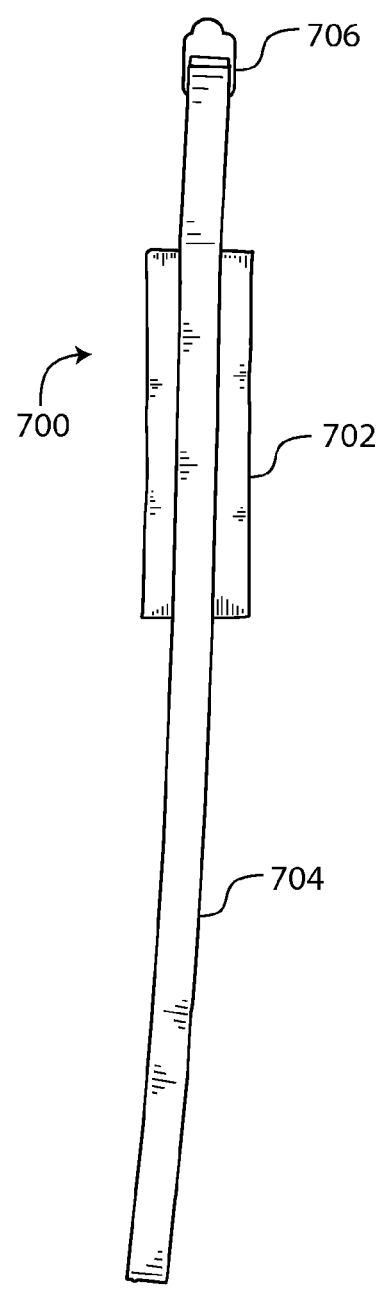

FIG. 25 illustrates a hand wrist support assembly, in the form of a hand/wrist sling assembly 700, in combination with the harness assembly and the rigid bar 108 of FIG. 16 shown worn by the wearer 102. For clarity, FIGS. 26A and 26B illustrate the front and back of the hand/wrist sling assembly 700 by itself Referring to FIGS. 25, 26A and 26B, the harness assembly includes a hand/wrist pad 702, a strap 704, and a double bar slide 706. The hand/wrist pad 702 can include a filler such as EVA foam, cotton, polyester fiber, or other cushioning material. The double bar slide 706 can be used to adjust the length of the strap and independently adjust a loop around the rigid bar 108. A side release, top release or cam buckle can be substituted for the double bar slide 706. In addition, a single bar slide can be substituted if only the strap's length adjustment is desired. Alternatively, the strap 704 can be fashioned into a loop by sewing, heat bonding, gluing, riveting, or otherwise bonding the strap to itself. A hook and loop fastener, for example, sold under the brand name Velcro, cab be used to removably secure the strap 704 to itself. The strap can also be similarly fashioned into two loops, a smaller loop that wraps around the rigid bar 108, and a larger loop that cradles the hand/wrist pad 702. While FIG. 25 illustrates the hand/wrist sling assembly 700 in combination with the harness assembly and the rigid bar 108 of FIG. 16, it should be understood by the reader, that the hand/wrist sling assembly 700 can be implemented in other embodiments, for example, the embodiments of FIGS. 4, and 10, 16, and 22, and can be adapted to be implemented in the embodiment of FIG. 24A.

Figure 27:
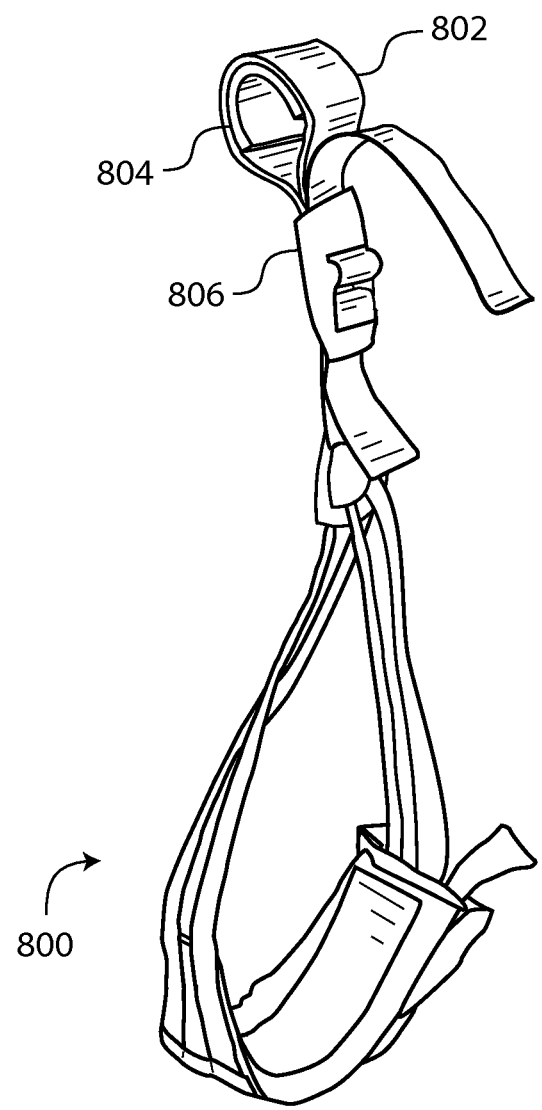
FIG. 27 illustrates a hand/wrist sling assembly with a frictional insert.

FIG. 27 illustrates a hand/wrist sling assembly 800 with a loop 802 for sliding along the rigid bar that includes a friction insert 804 within the loop 802. Suitable materials for the friction insert 804 include, but are not limited to, elastomers such as a synthetic or natural rubber. The friction insert 804 can be made of a material that has the property of slowing down or stopping the sliding of the hand/wrist sling assembly 800 along the bar when sufficient downward pressure is applied, typically, the downward pressure from the weight of holding a child. While the loop 802 is shown adjustable by double bar slide 806, the insert can be easily adapted into the other disclosed hand/wrist slings, for example, the hand/wrist sling assembly 106 of FIG. 7, the hand/wrist sling assembly 302 of FIG. 17, or the hand/wrist sling assembly 700 of FIG. 25. The friction insert 804 can be secured to the loop 802 by sewing, gluing, heat bonding, or by a hook and loop fastener. Alternatively, the friction insert 804 can surround the loop 802. The friction insert 804 can also be impregnated directly into the fabric of the loop 802.

Figure 28A:
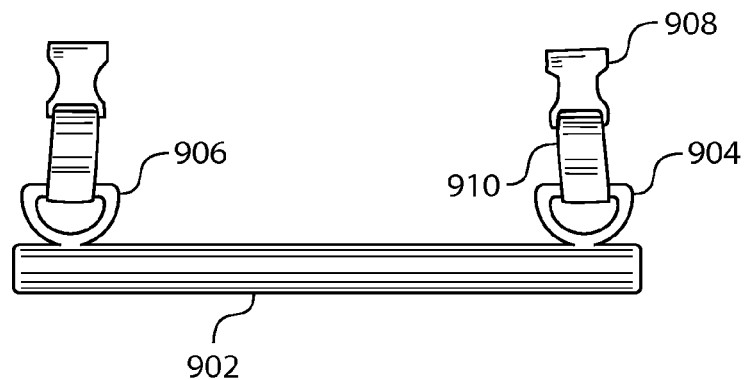
FIGS. 28A-28C illustrate rigid bars with integral end attachments.
Figure 28B:
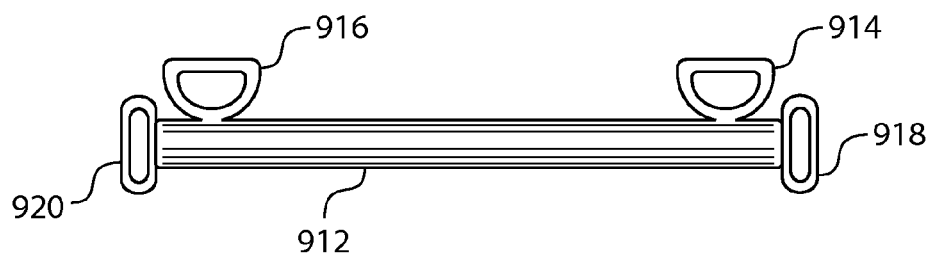
Figure 28C:
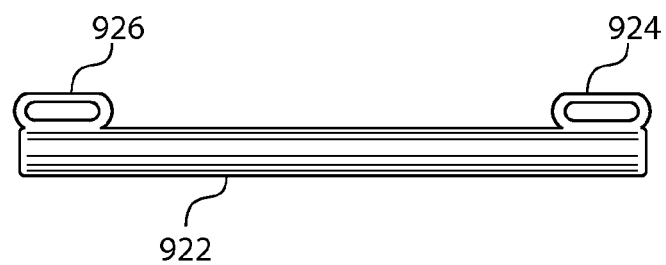

FIGS. 28A-28C each illustrate rigid bars with integral end attachments. FIG. 28A shows a rigid bar 902 with a first integral D-ring attachment 904 and a second integral D-ring attachment 906. A side release buckle 908 is secured to the first integral D-ring attachment 904 with a looped strap 910. FIG. 28B shows a rigid bar 912 with a first D-ring attachment 914 and a second D-ring attachment 916 secured to the top end portions of the rigid bar 912. A first rectangular loop attachment 918 and a second rectangular loop attachment 920 are secured to each end of the rigid bar 912. The first rectangular loop attachment 918 and the second rectangular loop attachment 920 are disposed to secure strap portions inline with the rigid bar 912. FIG. 28C shows a rigid bar 922 with a top attached first rectangular loop 924 and a top attached second rectangular loop 926.

In FIGS. 28A-28C, the rigid bars and their respective attachments can be integrally formed. For example, by casting in the case of metal rigid bar, or by molding thermoplastic or carbon fiber. The rigid bars and their respective attachments can alternatively be secured by welding, heat bonding, screwing, or riveting depending on the material. Those skilled in the art will readily recognize other means for securing the rigid bars with their respective attachments.

The rigid bars of FIGS. 28A-28C with their respective attachments can be coated with a protective material such as a rubberized coating. The attachments of FIGS. 28A-28C are illustrative of rigid bar and attachment combinations. Other attachment combinations can be made as appropriate.

Figure 29:
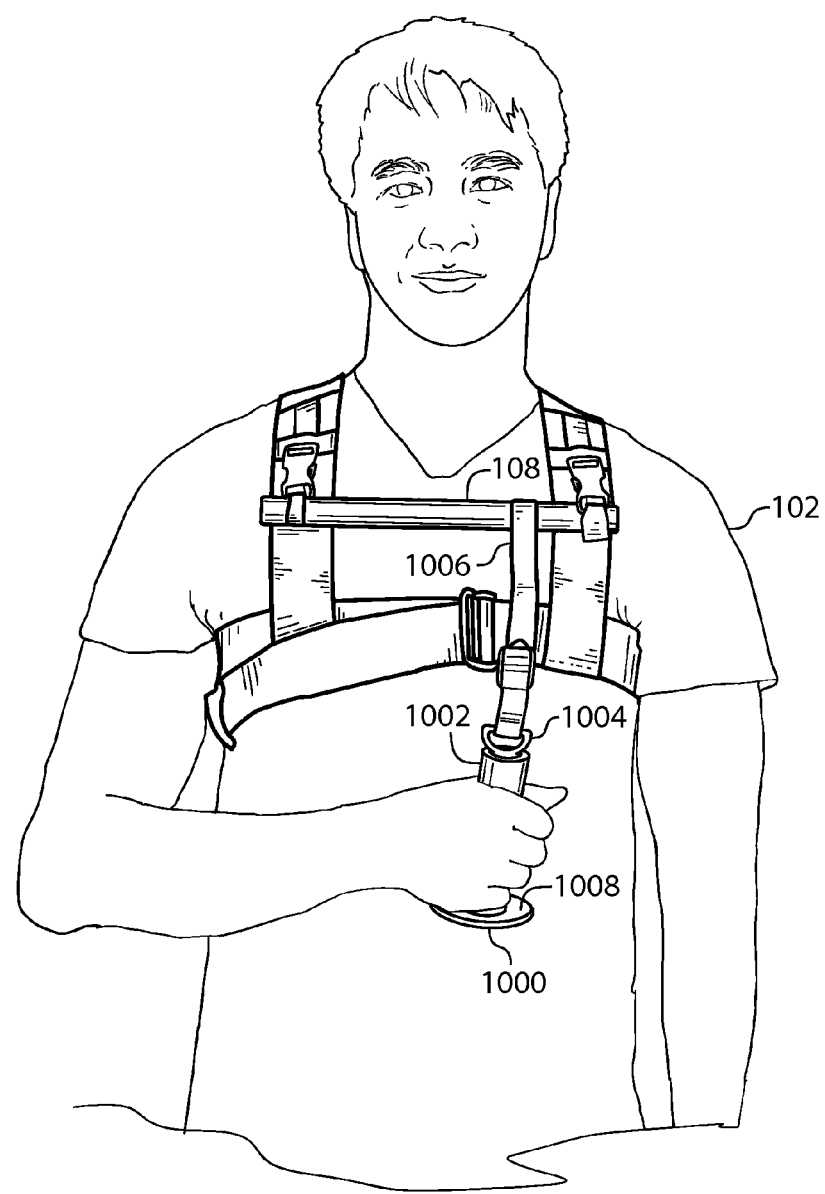
FIG. 29 illustrates a front view of a child carrier with an alternative hand/wrist support assembly as worn by the wearer.

FIG. 29 illustrates a hand/wrist support assembly 1000 slidable along the rigid bar 108 as worn by the wearer 102. The wearer 102 is depicted wearing a dual shoulder strap harness assembly similar to that of FIG. 16. This hand/wrist support assembly 1000 can also be used with dual shoulder strap harnesses of FIGS. 4, 10, and 22. A hand grip 1002 is secured via a D-ring 1004 to a hanging strap 1006. Alternatively, the hand grip 1002 can be secured to the hanging strap 1006 by a rectangular loop, a buckle or other securing interfaces capable of securing the hand grip 1002 to the hanging strap 1006 with sufficient strength to support the weight of a child. A portion of the hanging strap 1006 is looped and surrounds the rigid bar 108 so that the hand/wrist support assembly 1000 is slidable along the rigid bar.

Continuing to refer to FIG. 29, the wearer's hand is supported by a support base 1008 secured to the hand grip 1002. The hand grip 1002 can be made of plastic such as acrylonitrile butadiene styrene (ABS), or can be made of other materials such as aluminum, titanium, or carbon fiber. The hand grip 1002 and support base 1008 can be covered with a cushioning material such as ethylene propylene diene monomer (EPDM), nitrile foam, neophrene, or a low durometer ABS. The hand grip materials and the optional cushioning materials disclosed are meant to be examples. Those skilled in the art will readily recognize other materials suitable of both hand grips 1002 and hand grip cushioning. The support base 1008 can be integral to the hand grip 1002. Alternatively, the support base 1008 and the hand grip 1002 can be separate pieces secured together by fasteners, adhesive, or welding, depending on the support base and hand grip 1002 material.

Figures 30, 31:
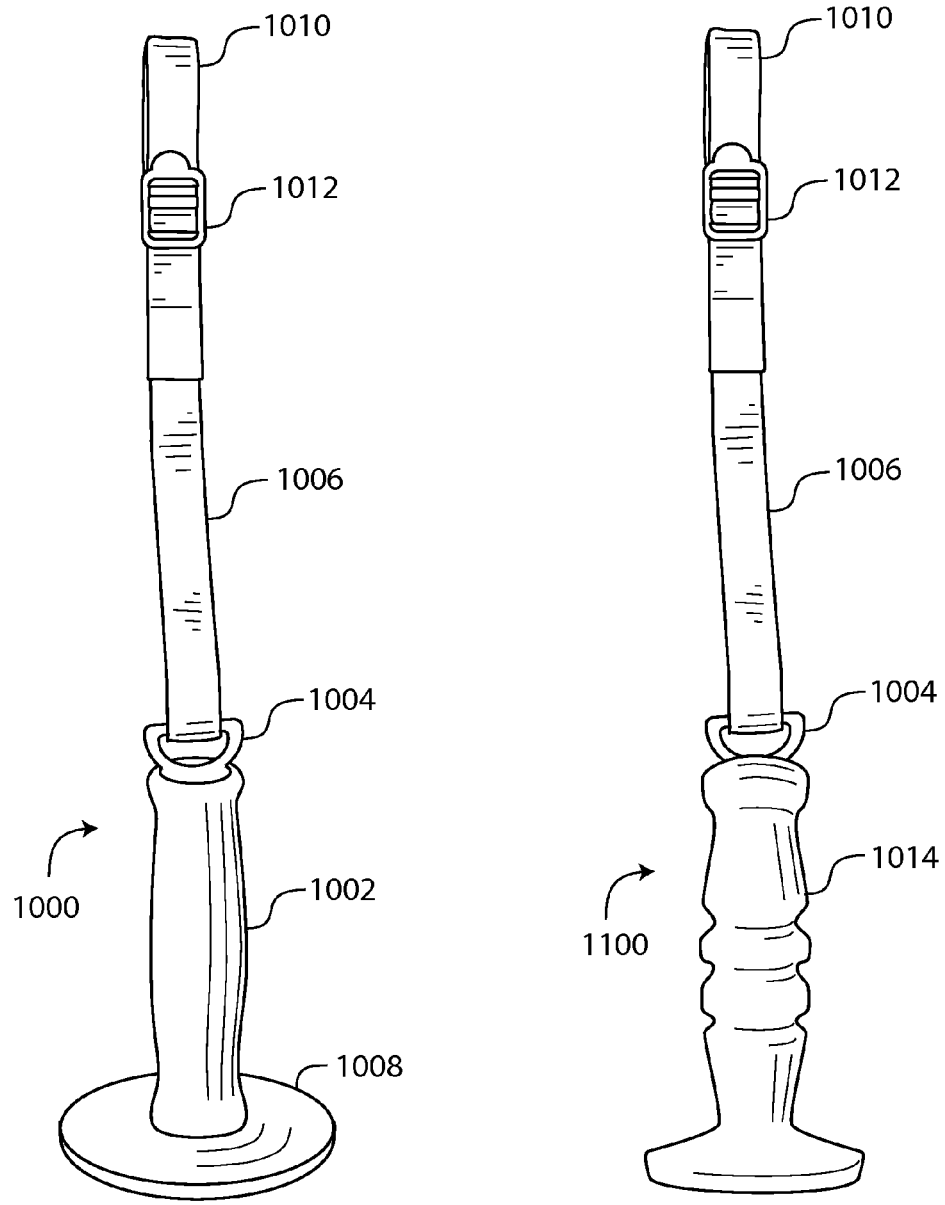
FIG. 30 illustrates the hand/wrist support assembly of FIG. 29.
FIG. 31 illustrates the hand/wrist support assembly of FIG. 29 with an alternative hand grip.

FIG. 30 illustrates the hand/wrist support assembly 1000 showing the hand grip 1002 secured to the support base 1008. The hanging strap 1006 is shown secured to the hand grip 1002 through the D-ring 1004 as previously described. The hanging strap 1006 is looped through a bar slide 1012 forming a hanging strap looped portion 1010. The hanging strap looped portion 1010 is disposed to slide along the rigid bar 108 of FIG. 29.

FIG. 31 illustrates a hand/wrist support assembly 1100 with a hand grip 1014 that includes an integral support base. The hand/wrist support assembly 1100 includes the hand grip 1014 with the integral support base. The hanging strap 1006 is secured to the hand grip 1002 through the D-ring 1004 as previously described. The hanging strap 1006 is looped through a bar slide 1012 forming a hanging strap looped portion 1010. The hanging strap looped portion 1010 is disposed to slide along the rigid bar 108 of FIG. 29.

Figure 32:
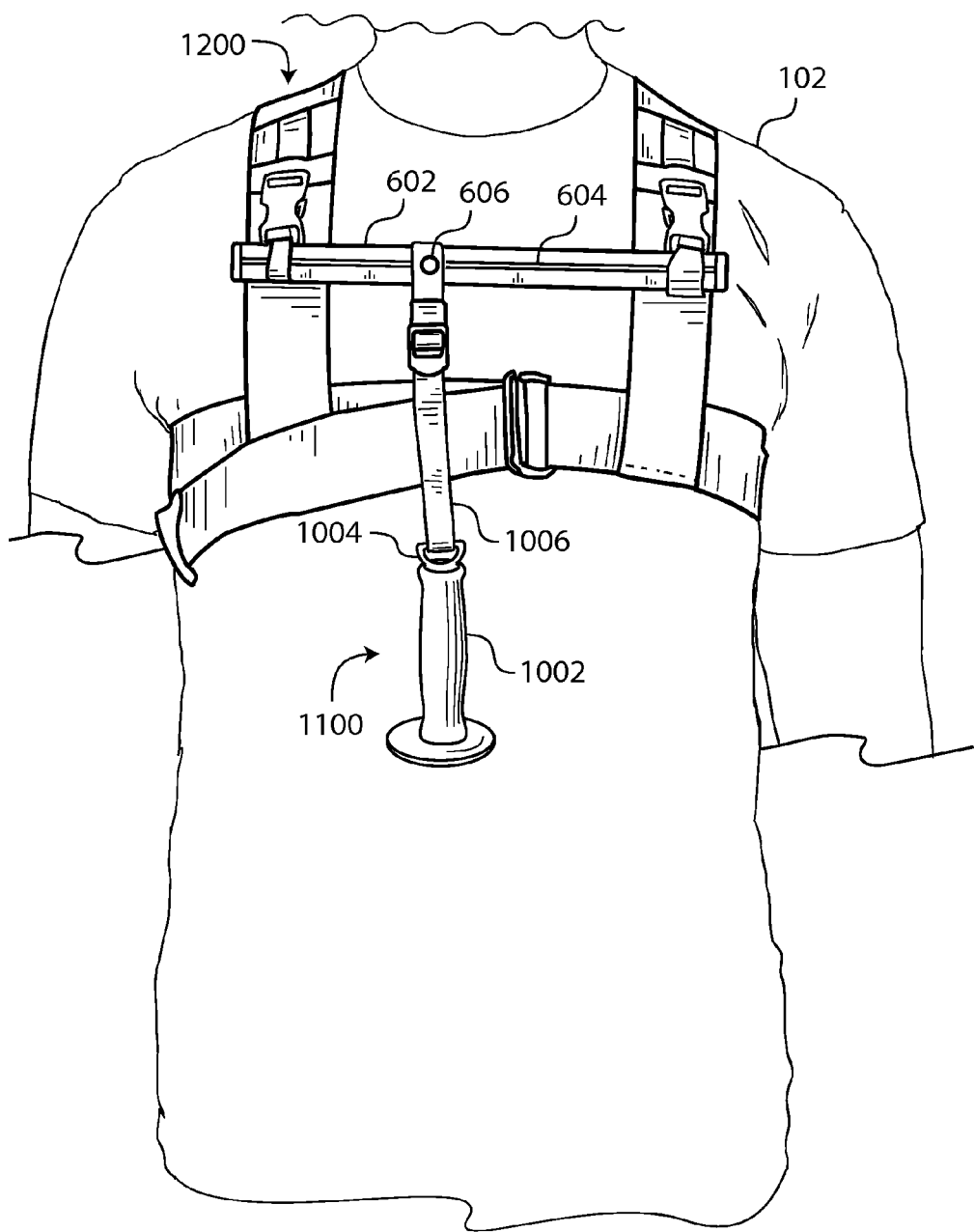
FIG. 32 illustrates the hand/wrist support assembly slidable along a slotted rigid bar.

FIG. 32 shows a child carrier 1200 worn by the wearer 102. The child carrier 1200 is substantially the same as the child carrier 600 of FIG. 24A except for hand/wrist support assembly 1100. The hand/wrist support assembly 1100 includes hand grip 1002, D-ring 1004, and hanging strap 1006 in cooperative relation as previously described for FIGS. 29 and 30. Hanging strap 1006 terminates with the flanged attachment 606. The flanged attachment 606 is cooperatively configured to slide along slot 604 of rigid bar 602 as previously described. While the child carrier 1200 utilizes the dual shoulder strap harness of FIG. 16, the hand/wrist support assembly 1100 in combination with the rigid bar 602 can easily be adapted to the dual shoulder strap harnesses of FIGS. 4, 10, and 22 based on the teachings of this disclosure.

An apparatus for carrying a child, infant, toddler, baby has been described. It is not the intent of this disclosure to limit the claimed invention to the examples, variations, and embodiments described in the specification. Those skilled in the art will recognize that variations will occur when embodying the claimed invention in specific implementations and environments. For example, the use of the term child carrying device or child carrier to characterize various embodiments is not meant to limit the use of the device to carrying children, toddlers, babies, or infants. As an additional example, the device may also be used to carry small animals or pets. In addition, it is possible to implement certain features described in separate embodiments in combination within a single embodiment. Similarly, it is possible to implement certain features described in single embodiments either separately or in combination in multiple embodiments. It is the intent of the inventor that these variations fall within the scope of the claimed invention. While the examples, embodiments, and variations are helpful to those skilled in the art in understanding the claimed invention, it should be understood that, the scope of the claimed invention is defined solely by the following claims and their equivalents.

What is claimed is:

1. A child-carrying device for assisting a wearer supporting a child on the wearer's arm, including:
   a dual-shoulder harness including a first shoulder strap portion extending over a first shoulder of the wearer and a second shoulder strap portion extending over a second shoulder of the wearer;
   a rigid bar positioned transversely across the front of the wearer's rib cage, the rigid bar secured to and holding apart the first shoulder strap portion and second shoulder strap portion at a position proximate to a first end portion of the rigid bar and a second end portion of the rigid bar; and
   a hand/wrist sling assembly slidable along the rigid bar.

2. The child-carrying device of claim 1 wherein the hand/wrist sling assembly further includes:
   a hanging strap with a loop portion cooperatively configured to slide along the rigid bar;
   a cushioned hand/wrist support, the cushioned hand/wrist support including a lateral angle with respect to the wearer; and
   a plurality of adjustment straps secured to the hanging strap and in captive relation with the cushioned hand/wrist support, and the plurality of adjustment straps adapted to adjust the lateral angle of the cushioned hand/wrist support.

3. The child-carrying device of claim 1, wherein:
   the first shoulder strap portion including a first strap end portion configured to loop over the wearer's back and under a first arm of the wearer and secured to the first end portion of the rigid bar; and
   the second shoulder strap portion including a second strap end portion configured to loop over the wearer's back and under a second arm of the wearer and secured to the second end portion of the rigid bar.

4. The child-carrying device of claim 3 further including a back strap detachably secured transversely across the wearer's back to the first shoulder strap portion and the second shoulder strap portion.

5. The child-carrying device of claim 3 further including:
   a fabric sleeve surrounding the rigid bar and including attachment portions securing the first strap end portion to the first end portion of the rigid bar and the second strap end portion to the second end portion of the rigid bar.

6. The child-carrying device of claim 3 including a plurality of strap coupling end attachments integral to the rigid bar.

7. The child-carrying device of claim 1 further including:
   the dual-shoulder harness further includes a transverse strap; and
   the first shoulder strap portion and the second shoulder strap portion are transversely secured below the rigid bar by the transverse strap.

8. The child-carrying device of claim 7 further including a plurality of adjustable strap portions laterally engaging the transverse strap to each end of the rigid bar.

9. The child-carrying device of claim 7 further including a back strap detachably secured transversely across the wearer's back to the first shoulder strap portion and the second shoulder strap portion.

10. The child-carrying device of claim 7 wherein the hand/wrist sling assembly further includes:
    a hanging strap with a loop portion cooperatively configured to slide along the rigid bar;
    a cushioned hand/wrist support, the cushioned hand/wrist support including a lateral angle with respect to the wearer; and
    a plurality of adjustment straps secured to the hanging strap and in captive relation with the cushioned hand/wrist support, and the plurality of adjustment straps adapted to adjust the lateral angle of the cushioned hand/wrist support.

11. The child-carrying device of claim 1, wherein:
    the dual-shoulder harness further includes a transverse strap;
    the first shoulder strap portion and the second shoulder strap portion are transversely and removably secured below the rigid bar by the transverse strap;
    the first shoulder strap portion and the second shoulder strap portion form a cross-strap across the wearer's back; and
    the rigid bar is detachably attached to at least one of the first shoulder strap portion or the second shoulder strap portion.

12. The child-carrying device of claim 11 wherein the hand/wrist sling assembly further includes:
    a hanging strap with a loop portion cooperatively configured to slide along the rigid bar;
    a cushioned hand/wrist support, the cushioned hand/wrist support including a lateral angle with respect to the wearer; and
    a plurality of adjustment straps secured to the hanging strap and in captive relation with the cushioned hand/wrist support, and the plurality of adjustment straps adapted to adjust the lateral angle of the cushioned hand/wrist support.

13. The child-carrying device of claim 1 further including:
    a flanged attachment affixed to the hand/wrist sling assembly; and the rigid bar includes a slot along its length disposed to receive and hold a portion of the flanged attachment making the hand/wrist sling assembly slidable along the slot.

14. The child-carrying device of claim 1 wherein the hand/wrist sling assembly further including, a friction insert configured to engage the rigid bar.

\* \* \* \* \*